United States Patent
Selzer et al.

(10) Patent No.: US 7,074,187 B2
(45) Date of Patent: Jul. 11, 2006

(54) SYSTEM AND METHOD FOR IMPROVING ULTRASOUND IMAGE ACQUISITION AND REPLICATION FOR REPEATABLE MEASUREMENTS OF VASCULAR STRUCTURES

(76) Inventors: Robert H. Selzer, 634 N. McCadden Pl., Los Angeles, CA (US) 90004; Howard N. Hodis, 1212 Milan Ave., South Pasadena, CA (US) 91030

( * ) Notice: Subject to any disclaimer, the term of this patent is extended or adjusted under 35 U.S.C. 154(b) by 0 days.

(21) Appl. No.: 10/319,382

(22) Filed: Dec. 13, 2002

(65) Prior Publication Data
US 2004/0116812 A1   Jun. 17, 2004

(51) Int. Cl.
*A61B 8/00* (2006.01)
(52) U.S. Cl. .................................................. 600/440
(58) Field of Classification Search ........ 600/440–441, 600/443, 447, 453–458; 128/916; 382/128
See application file for complete search history.

(56) References Cited
U.S. PATENT DOCUMENTS

| | | | |
|---|---|---|---|
| 5,181,513 A * | 1/1993 | Touboul et al. | 600/443 |
| 5,495,852 A * | 3/1996 | Stadler et al. | 600/443 |
| 6,132,373 A | 10/2000 | Ito et al. | |
| 6,402,693 B1 * | 6/2002 | Emery | 600/443 |
| 6,450,959 B1 * | 9/2002 | Mo et al. | 600/441 |

\* cited by examiner

Primary Examiner—Francis J. Jaworski

(57) ABSTRACT

High resolution B-mode ultrasound images of the common carotid artery are obtained with an ultrasound transducer using a standardized methodology. Subjects are supine with the head counter-rotated 45 degrees using a head pillow. The jugular vein and carotid artery are located and positioned in a vertical stacked orientation. The transducer is rotated 90 degrees around the centerline of the transverse image of the stacked structure to obtain a longitudinal image while maintaining the vessels in a stacked position. A computerized methodology assists operators to accurately replicate images obtained over several spaced-apart examinations. The methodology utilizes a split-screen display in which the arterial ultrasound image from an earlier examination is displayed on one side of the screen while a real-time "live" ultrasound image from a current examination is displayed next to the earlier image on the opposite side of the screen. By viewing both images, whether simultaneously or alternately, while manually adjusting the ultrasound transducer, an operator is able to bring into view the real-time image that best matches a selected image from the earlier ultrasound examination. Utilizing this methodology, measurement of vascular dimensions such as carotid arterial IMT and diameter, the coefficient of variation is substantially reduced to values approximating from about 1.0% to about 1.25%. All images contain anatomical landmarks for reproducing probe angulation, including visualization of the carotid bulb, stacking of the jugular vein above the carotid artery, and initial instrumentation settings, used at a baseline measurement are maintained during all follow-up examinations.

22 Claims, 12 Drawing Sheets

SYSTEM AND METHOD FOR IMPROVING ULTRASOUND IMAGE ACQUISITION AND REPLICATION FOR REPEATABLE MEASUREMENTS OF VASCULAR STRUCTURES

STATEMENT REGARDING FEDERALLY FUNDED R&D

The invention described herein was made in performance of work under a NASA Contract, and is subject to the provisions of Public Law 96-517 (35 USC 202) in which the Contractor has elected to retain title.

CROSS REFERENCE TO RELATED APPLICATIONS

The present application is related to and takes priority from U.S. provisional patent application Ser. No. 60/279,229, filed Mar. 27, 2001, entitled MOTORIZED ROTATOR DEVICE FOR ULTRASOUND PROBE, and is further related to co-pending U.S. Patent applications entitled SPLIT-SCREEN DISPLAY SYSTEM AND STANDARDIZED METHODS FOR ULTRASOUND IMAGE ACQUISITION AND MULTI-FRAME DATA PROCESSING, SPLIT-SCREEN DISPLAY SYSTEM AND STANDARDIZED METHODS FOR ULTRASOUND IMAGE ACQUISITION AND PROCESSING FOR IMPROVED MEASUREMENTS OF VASCULAR STRUCTURES, and MOTORIZED ULTRASOUND TRANSDUCER FOR REPEATABLE MEASUREMENTS OF VASCULAR STRUCTURES, all filed on instant date herewith, all commonly owned by the assignee of the present invention, the entire contents of all of which are expressly incorporated herein by reference.

FIELD OF THE INVENTION

The present invention is directed to the field of ultrasonographic vascular visualization and vascular structure measurements and, more particularly, to standardized, reliable and reproducible ultrasonographic vascular imaging and structural measurements including intima-media thickness and vessel diameter determinations to yield anatomical and physiologic measurements.

BACKGROUND OF THE INVENTION

Cardiovascular disease remains the leading cause of morbidity and mortality in industrialized nations. An increase in arterial wall stiffness and thickness is the common pathological pathway for the factors that lead to initiation and progression of the vascular changes associated with cardiovascular disease. Functional disturbances of the vascular wall may occur early in the artherosclerotic process, even before the anatomical changes of intima-media thickening become perceptible. Therefore, study of dynamic and anatomic arterial wall properties of large arteries, such as the carotid and femoral arteries has become commonplace. Since the mechanical and structural properties of the arterial wall may change before the occurrence of clinical symptoms of cardiovascular disease, the non-invasive measurements of arterial wall properties has become common in the study of atherosclerosis and as an extremely important method for identifying individuals at risk for cardiovascular events. Therefore, standardized, improved and easily deployed methods for evaluating arterial wall structures and characteristics has important implications leading to earlier and more effective strategies for screening, prevention and treatment of atherosclerosis and cardiovascular disease.

Direct measurement of the arterosclerotic burden and its rate of progression can be determined by quantitative imaging of vascular structures. The only standardized imaging methodology currently available to determine coronary and cerebrovascular atherosclerosis is angiography. However, this imaging technique is limited to luminal dimensions and only inferences about the extent of arterial wall involvement can be made. Further, since angiographic procedures are invasive, they cannot be performed in asymptomatic persons. Additionally, angiographic measurement of atherosclerosis is a relatively high variability procedure. As such, coronary angiography has no applicability in the screening for and in the prevention of atherosclerosis and cardiovascular disease. Other than B-mode ultrasonography, there is no reliable non-invasive technique available to directly measure atherosclerosis or its progression.

Accordingly, high resolution B-mode ultrasonography can be used to non-invasively and quantitatively image the atherosclerotic process in peripheral vessels reflective of coronary artery and cerebrovascular atherosclerosis. Measurement of carotid arterial wall stiffness and intima-media thickness (IMT) have been shown to reflect early subclinical atherosclerosis. Large epidemiologic and case-control studies have demonstrated an association between carotid arterial wall stiffness and IMT, measured by B-mode carotid ultrasonograpy, and cardiovascular, cerebrovascular and atherosclerosis risk factors in both men and women. The association between coronary and carotid atherosclerosis depends in part on exposure of both arterial beds to the same risk factors. Studies have demonstrated a strong relationship between carotid arterial wall stiffness and IMT and angiographic presence, extent, and progression of coronary artery disease in both men and women. Arterial wall thickness demonstrates as good or better correlation with coronary artery disease than does traditional lipid and non-lipid risk factors. Most importantly, carotid arterial wall stiffness and thickness predict clinical cardiovascular and cerebrovascular events in men and women.

Since the lumen-intima and media-adventitia echoes in carotid ultrasound images were first identified and histologically verified as an accurate measure of intima-media thickness of the arterial wall, B-mode ultrasonography has been used for non-invasive quantitative measurement of intima-media thickness (IMT) as a direct measurement of atherosclerosis. The methodology used to measure IMT has relied on human visual judgment in order to manually identify echo coordinates indicating the lumen-intima and media-adventitia boundaries. The accuracy, reproducibility and precision of IMT measurements, determined by manual identification methods, are limited by human variability in the operation of coordinate designation devices and by the resolution of the displayed ultrasound image.

Recently, certain automated IMT measurement techniques have become available which improve the accuracy and precision of such measurements. However, even though absolute IMT measurements are improved by automated techniques, measurement of changes in arterial IMT and diameter over time, which indicates progression or regression of atherosclerosis, must also be accurate, and repeatable in both time and space. Carotid images, acquired in different examinations, must be precisely replicated since very small changes in the ultrasound view of the artery can cause large changes in the IMT or diameter measurements.

While standardized positioning procedures assist in minimizing changes, a patient's position on the examination table can rarely be reproduced exactly in different examinations. Thus, identical images cannot be obtained under these conditions. Attempts to superimpose images from different examinations using color coding or image subtraction have not been successful for both technical and procedural reasons since small differences in image acquisition, which are always present, as discussed above, are exaggerated in the superimposed color coded or subtracted images, making interpretation difficult at best. These image differences are driven by the limited reproducibility image acquisition techniques currently available.

The need for a standardized methodology by which carotid artery images are acquired and IMT and arterial dimensions are measured in an accurate and reproducible form will become apparent when it is recognized that ultrasonography has distinct advantages over any of the other techniques currently available for evaluating carotid arterial vascular structures such as the intima-media thickness and diameter, and physiologic structures such as arterial wall stiffness as cumulative measures of generalized atherosclerosis. In particular, high resolution B-mode ultrasonography is readily available to practitioners. It is inexpensive, easy to perform, poses no risk, and can be repeated as frequently as desired. Most importantly, it can be used in healthy, asymptomatic individuals to determine the extent and progression of atherosclerosis. Accurate determination of carotid arterial anatomy (IMT and diameter measurements) and physiology (stiffness and compliance) is possible, with the entire process of carotid artery image acquisition and measurement taking approximately 30 minutes.

Utilizing this technique, measurement of the rate of atherosclerosis progression can be envisioned as part of a yearly physical examination. Although readily employed as the most common measure of atherosclerosis progression in clinical trials and human studies, further standardization of this methodology for application in screening, prevention and treatment of atherosclerosis and cardiovascular and cerebrovascular disease is still required.

This needs to be accomplished at the earliest time possible, such that practitioners can more accurately and cost-effectively screen individuals at risk for a cardiovascular or cerebrovascular event and to design therapies on an individual basis in the prevention and treatment of atherosclerotic disease.

SUMMARY OF THE INVENTION

In one aspect of the invention, a standardized method for obtaining an accurate and reproducible vascular characteristic measurement comprises performance of an ultrasonographic examination of vascular structures and capturing ultrasonographic images under a standardized procedure.

In one aspect of the standardized imaging acquisition procedure, a current image in real-time is visually compared with a recalled image acquired in a previous examination on a split-screen display system. The previous ultrasound image is recalled and displayed on a first-half portion of a split-screen display during performance of a current examination. An ultrasonographic image of the same vascular structures is displayed in real-time on a second-half portion of the split-screen display. During the course of the present ultrasound examination, the image in real-time is visually compared to the recalled image and the ultrasonographic transducer orientation is adjusted until the current image substantially matches the recalled image.

A system for obtaining accurate and reproducible images and measurements of vascular structures comprises a high resolution ultrasound system operating in B-mode and includes a high frequency transducer, the transducer developing ultrasound images in a plane oriented in accord with a major axis of the transducer. An image recording system receives and records images captured by the ultrasound system and a computer processor, including an image digitizer, is coupled to the ultrasound system and the image recording system. The computer processor displays digitized ultrasound images on a split-screen display.

An image acquisition/analysis application, hosted on the computer processor, receives a stored digitized ultrasound image taken during a previous examination and allocates the retrieved image to a first screen location of the split-screen display. The image acquisition/analysis application then allocates a digitized ultrasound image taken during a present ultrasound examination to a second screen location of the split-screen display. An operator compares the two views so as to match the real-time ultrasound image, taken during a present ultrasound examination procedure, to the retrieved stored ultrasound image taken during a previous examination procedure.

In a further aspect of the invention, a standardized method for accurately replicating ultrasound images of vascular structure, taken at spaced-apart examination intervals, so as to develop a set of substantially congruent sequential images of vascular structure, comprises the steps of orienting an individual such that a the neck is exposed after the head is counter-rotated about 45 degrees with a head positioning apparatus, and positioning an ultrasound transducer so as to capture a transverse image view through a neck section that contains the carotid artery and jugular vein. The transverse view is displayed on a split-screen display and transducer position and angulation are manipulated until the jugular vein and carotid artery are displayed in a substantially vertical stack orientation with the jugular vein above the carotid artery, the stack orientation defining an approximate vertical axis through a center of the jugular vein and a center of the carotid artery. The transducer is then rotated around the central image line (the vertical axis) through approximately 90 degrees, so as to capture a longitudinal image view along a length of the carotid artery while maintaining the jugular vein stacked above the carotid artery.

Particular features of the standardized method of the invention include displaying the longitudinal image view of the jugular vein stacked above the carotid artery, in real-time, on a first half portion of a split-screen display and retrieving a stored longitudinal image view of the jugular vein stacked above the carotid artery taken during a previous ultrasound examination and displaying the previous longitudinal image on a second half portion of the split-screen display. Transducer position is further manipulated so as to bring the real-time longitudinal view into congruence with the retrieved longitudinal view by visual comparison of the first and second half portions of the split-screen display.

Advantageously, each longitudinal view of the carotid artery includes an image of a portion of a carotid artery bulb structure, each longitudinal view further including an image of at least a length of a far wall portion of the carotid artery distal to the carotid bulb. Further, a set of display characteristic parameters, such as ultrasound settings, associated with acquisition of the previous longitudinal image from a previous ultrasound examination are retrieved and the set of display characteristic parameters are displayed for the repeat ultrasound examination and replicated in real-time. In other words, instrumentation acquisition parameters are replicated from one examination to another within the same individual.

In a particular aspect, the invention comprises a standardized method for acquiring reproducible ultrasound images and performing standardized and reproducible intima-media thickness (IMT) and vascular structure measurements, the measurements taken in substantially the same location of the carotid artery in each of a plurality of time-spaced-apart examinations. A first ultrasound image of a longitudinal section of a carotid artery is obtained, the image including a carotid artery bulb portion as a reference location. An intima-media thickness (IMT) measurement is performed on an arterial wall portion of the carotid artery distal to the carotid bulb and the first ultrasound image is stored as a prior ultrasound examination image in a memory store. Arterial lumen dimensions are also measured over the same arterial wall segment as the IMT measurement.

Subsequently, a second ultrasound image of a longitudinal section of a carotid artery is obtained, with the image including the carotid bulb portion as a reference location. The second image is displayed in one portion of a split-screen display and the first image, retrieved from the memory store, is displayed in another portion of the split-screen display. The ultrasound transducer is manipulated until the second image visually matches the first image.

A computer processing system, in accordance with the invention, develops vascular characteristic measurements from ultrasound images and comprises a video recorder, the recorder storing vascular ultrasound images taken during the course of an ultrasound examination procedure. A mass data storage memory unit stores vascular ultrasound images taken during the course of a previous ultrasound examination procedure, a digitizing and image processing system, and a computer processing unit coupled to the video recorder, mass data storage memory unit, and digitizing system. A split-screen display system, coupled to the computer processing unit, displays a digitized vascular ultrasound image retrieved from the memory storage unit on one side of the split-screen display and displays a digitized vascular ultrasound image taken from the video recorder on the other side of the split-screen display.

Advantageously, the computer processing system includes an analysis engine hosted on the computer processing unit, the analysis engine including means for establishing an approximate boundary location of a first interface region of a portion of an arterial wall structure, means for establishing an approximate boundary location of a second interface region of said portion of the arterial wall structure, and means for establishing an actual interface edge, for the first and second interface regions, within a plane region centered about the corresponding approximate boundary location. A vascular characteristic calculation engine returns vascular characteristic measurement calculations, such as IMT and lumen dimensions, made with respect to the actual interface edges of the first and second interface regions.

DESCRIPTION OF THE DRAWINGS

These and other features, aspects and advantages of the present invention will be more fully understood when considered with respect to the following specification, appended claims, and accompanying drawings wherein:

DESCRIPTION OF THE INVENTION

Figure 1:
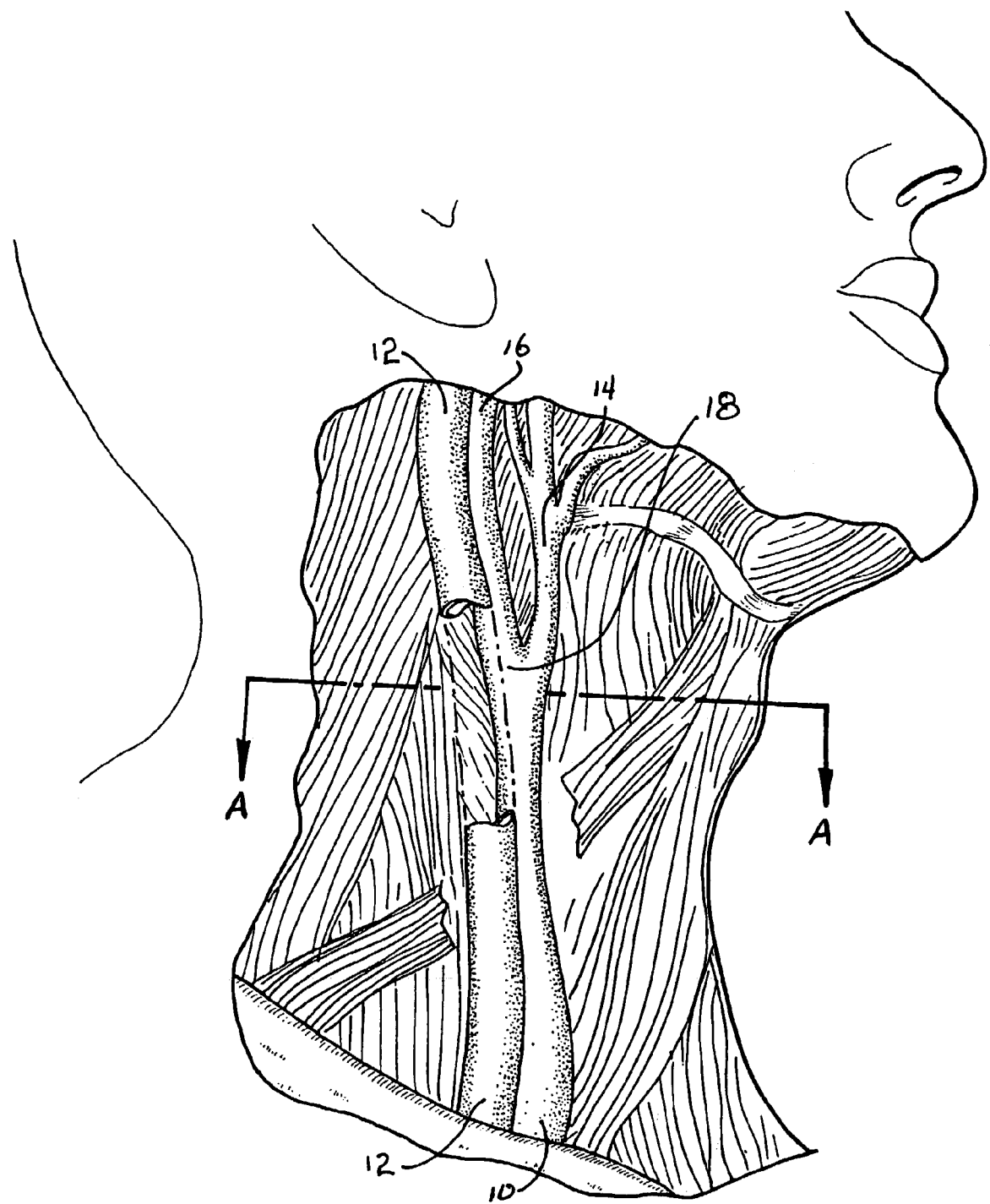
FIG. 1 is a simplified illustration of a superficial dissection of the right side of the neck, showing the right common, internal and external carotid arteries and jugular vein in their approximate anatomical positions.

B-mode ultrasound has gained popularity as a non-invasive method for direct visualization of superficial vessels. With B-mode ultrasound, intima-media thickness (IMT) and arterial stiffness can be directly measured since image acquisition of the arterial wall thickness and vessel diameter can be obtained simultaneously in a dynamic fashion throughout the cardiac cycle. The present invention relates generally to a standardized method of carotid artery B-mode ultrasound image acquisition with a computerized split-screen system, and carotid arterial diameter and intima-media thickness (IMT) measurements from B-mode ultrasound images which utilizes computerized edge tracking. Multi-frame image processing automatically measures arterial diameter and IMT in multiple sequential frames spanning several cardiac cycles. Further, in accordance with the invention, a computerized methodology assists operators to accurately replicate images obtained from a particular individual over several spaced-apart examinations. The methodology utilizes a split-screen display in which the arterial ultrasound image from an earlier examination is displayed on one half of the screen while a real-time "live" ultrasound image from a current examination is displayed next to the earlier image on the other half of the screen. By viewing both images, whether simultaneously or alternately, while manually adjusting the ultrasound transducer, an operator is able to bring into view the real-time image that best matches a selected image from the earlier ultrasound examination. Utilizing this methodology, measurement of vascular dimensions such as carotid arterial IMT and diameter, the coefficient of variation is substantially reduced to values approximating from about 1.0% to about 1.25%.

In a summarized form, the present invention concerns video ultrasound signals, obtained either directly from a commercially available ultrasound imaging system, or from a VCR playback of prerecorded video signals, which are directed through an image digitization system configured on a personal computer (PC). Ultrasound images are continuously digitized in real-time and displayed on one side of a computer graphical split-screen display. During an initial ultrasound examination, an operator views the computer display with the ultrasound transducer positioned so as to visualize the carotid artery. When the computer display shows a carotid artery image that is considered suitable for IMT or arterial diameter measurements, the operator right-clicks a mouse which interrupts the digitization process and stores the digital image appearing on the screen at that time as a "selected" digital image.

During a second or subsequent examination, the stored image from the first examination is displayed on one half of a computer's graphical split-screen display, while the above-described procedure is utilized in order to capture the real-time arterial image controlled by an operator's movement of the transducer, on the other half of the screen. When the image from the present examination best matches the image from the previous examination, the operator "clicks" a mouse, as previously described, to identify and store the new present examination image.

Following image capture of a single frame, arterial diameter or IMT is measured as a two frame average. If a sequence of sequential frames are captured, the dynamic mechanical properties of the arterial wall are dynamically measured over several cardiac cycles with a computerized edge tracking, multi-frame processing methodology that measures arterial diameter and IMT in multiple sequential frames. Carotid arterial diameter and IMT dimensions, measured in B-mode ultrasonograms, by computerized edge tracking, multi-frame processing are highly reproducible, particularly when it is understood that arterial wall properties are measured in substantially the same place, over the same distance, on an individual-by-individual basis, even over multiple examinations ranging over a period of months to years. The accuracy and reproducibility of the standardized image acquisition methodology, as well as the computerized edge tracking, multi-frame processing methodology function, in combination, to define a non-invasive, inexpensive, simple to use system which is well within the capabilities of practitioners or other caregivers.

FIG. 1 illustrates a superficial dissection of the right side of a human neck, so as to show the position of the right common carotid artery 10 and the jugular vein 12. As is well understood by those having skill in the art of anatomy, the jugular vein is external to, runs alongside, and overlays, for at least a portion of its length, the carotid artery. For purposes of illustration and ease of explanation, the jugular vein is depicted in the exemplary embodiment of FIG. 1 as having been resected in order to expose a portion of the carotid artery beneath it.

The carotid artery 10 traverses from the torso to the neck in the region of the fore portion of the clavicle, proximate the thyroid gland. The common carotid portion ascends the neck until it bifurcates into an external carotid branch 14 and internal carotid branch 16, at a location that is near (but could be somewhat above or below) the corner of the mandible. The region where the common carotid 10 branches into the external carotid 14 and internal carotid 16 includes a region termed the carotid bulb 18. The carotid bulb 18 is that portion of the common carotid 10 where the arterial diameter increases in order to form a "bulb" shape, just before the common carotid artery branches into the internal and external carotid arteries.

Recognizing the carotid artery bulb 18 is a particularly important feature of the present invention, since it is a distinctive feature which can be visualized during image acquisition by B-mode ultrasonography, and which provides a convenient structural reference point for an operator's location, longitudinally, along the common carotid artery. In a manner that will be described in greater detail below, visualization of the carotid bulb 18 allows an operator to define a physical location along the arterial wall in relation to the carotid bulb at which arterial wall characteristic measurements may be performed on a repeatable basis. Performing a repeated measurement at a standardized location (i.e., approximately 0.5 centimeters below the inception of the carotid bulb, in a direction opposite blood flow).

In the course of an arterial visualization process, in accordance with the present invention, high resolution B-mode ultrasound images of the right or left common carotid artery are obtained utilizing a 7.5 to 10 MHz linear array sonogram transducer coupled to a conventional ultrasound apparatus. Patients are placed in a supine position, with the head rotated approximately 45° to the left or right, using a 45° head pillow; in an aspect approximated by the illustration of FIG. 1 (the embodiment FIG. 1 depicts the head rotated approximately 45° to the left).

The transducer is initially positioned to develop a transverse view of the region of the neck including the jugular vein and carotid artery. Such a transverse view might be developed along a transverse plane indicated by the line AA in FIG. 1. The jugular vein 24 and carotid artery 26 are located in the transverse view with the jugular vein stacked above the carotid artery, as illustrated in the exemplary cross-sectional anatomical diagram of FIG. 2, taken along plane AA of FIG. 1. With regard to FIG. 2, it should be understood that an ultrasound transducer operating in the 7.5–10 MHz range captures an image from the point of contact (i.e., at the transducer/epidermis interface) to about 3 to 5 centimeters (typically from about 4.0 to about 4.5 centimeters) within the neck tissue. Thus, the image seen on an operator's split-screen display (represented by FIG. 2) would suitably comprise the epidermal layer 20 at the top of the screen and a region of soft tissue 22 below the epidermal layer 20 and intermediate the epidermal layer and the jugular vein 24. The lumen of the jugular vein 23 necessarily appears circular and is substantially darker in color than the surrounding tissue, making it quite easy to visualize sonographically. Just beneath the jugular vein 24 the common carotid artery 26 also appears as an object having a dark, circular lumen 25 surrounded by lighter or brighter colored soft tissue 27, termed the intima-media complex. If the patient's head was positioned correctly, at the appropriate 45° deflection, the transverse sonographic view should show the jugular vein 24 positioned directly above the common carotid artery 26.

Figure 2:
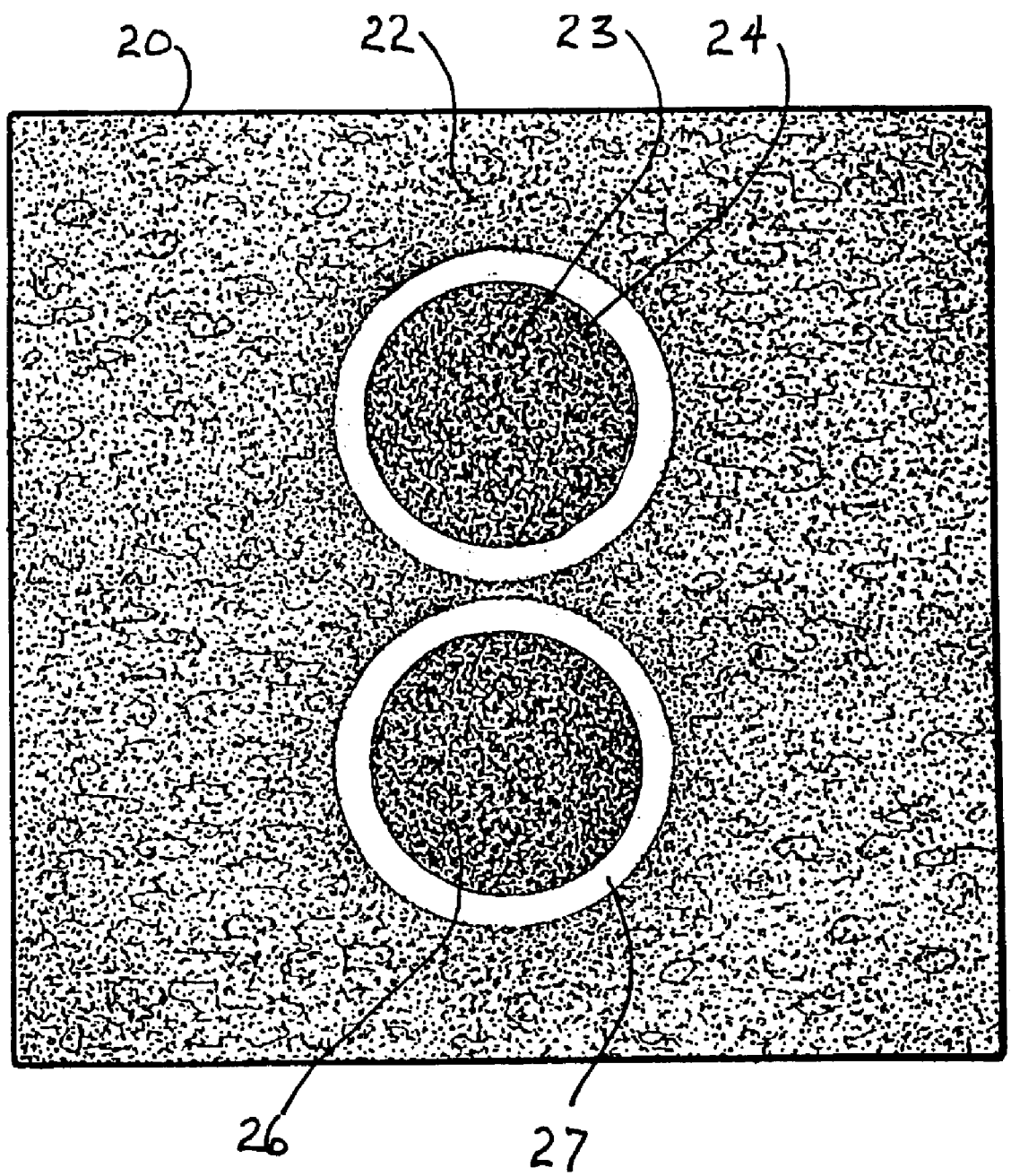
FIG. 2 is a simplified illustration of jugular vein/carotid artery stacking, taken along the transverse plane AA of FIG. 1.

In the exemplary embodiment of FIG. 2, the jugular vein is depicted as outlined by a lighter colored wall complex. Those familiar with ultrasound visualizations of the jugular vein will recognize that the jugular vein appears as dark colored structure with little circumferential delineation. The jugular vein, 24 is outlined in FIG. 2 only for purposes of clarity of identification and ease of explanation, and not as any indication of structure.

Care is taken to position the transducer in a way that displays the jugular vein and carotid artery images stacked, jugular vein above the carotid artery to bring the central image line of the jugular vein 24 and carotid artery 26 into substantial vertical alignment in the sonographic transverse image plane. Bringing the jugular vein into a stacked alignment with the carotid artery is a particularly important feature of the methodology of the present invention, since it allows for establishment of a standardized, repeatable reference position from which all subsequent transducer manipulations are made. It is also important to bring the stacked jugular/carotid structure to the center of the transverse sonographic image, for reasons that will be explained in greater detail below.

Once the jugular and carotid are located in the transverse view, with the jugular vein stacked above the carotid artery, the transducer is rotated 90° around the central image line of the transverse image of the stacked jugular vein/carotid artery, in order to obtain a longitudinal image, while maintaining the two vessels in the stacked position. An illustration of a longitudinal view, through a longitudinal section of the right common carotid artery and jugular vein, following transducer rotation, in accordance with practice of principles of the invention, is shown in FIG. 3A.

Capturing an ultrasound image in this fashion, allows for a very consistent and standardized method for image acquisition of the longitudinal view of the carotid artery, such that tangential thickness perturbations are substantially minimized, if not eliminated. Obtaining a longitudinal section (view) of a cylindrical vessel farther and farther off-axis, results in substantially increasing wall thicknesses and an apparent decrease in arterial diameter, with increasing displacement outwardly from the vessel's central axis. In order to obtain repeatable images for repeatable measurements of the arterial wall thickness and arterial diameter from a cylindrical vessel, the longitudinal view must be necessarily obtained, if not along the axis, then at least at a known and reproducible position displaced from the axis. Initially stacking the jugular vein and carotid artery in the initial transverse view, and aligning the stacked structure in the center of the image field, allows for repeatable longitudinal imaging, at the axis, with a simple 90° rotation of the transducer around the central image line.

As will be described in greater detail below, variability in transducer rotation techniques are substantially reduced, if not eliminated, by creating a fixed reference position for rotation, at the time of transverse view acquisition. This can be assisted when the ultrasound transducer is configured in a holder that rotates in a cylindrical housing. The housing of the ultrasound probe rotator device rests on the neck of the subject and acts as an anchor or fixed reference point. The holder is coupled for precise rotation by a stepper motor, for example. The operator need only manually manipulate the transducer in order to develop the appropriate transverse view, and then activate the motorized holder, which rotates the transducer through 90°, with respect to a fixed reference position. Thus, so long as the operator is able to reproduce the stacked, transverse image of the jugular vein/carotid artery complex, the motorized rotator device/transducer automatically and repeatedly develops the appropriate longitudinal image along a reproducible plane of the cylindrical vessel.

Figure 3A:
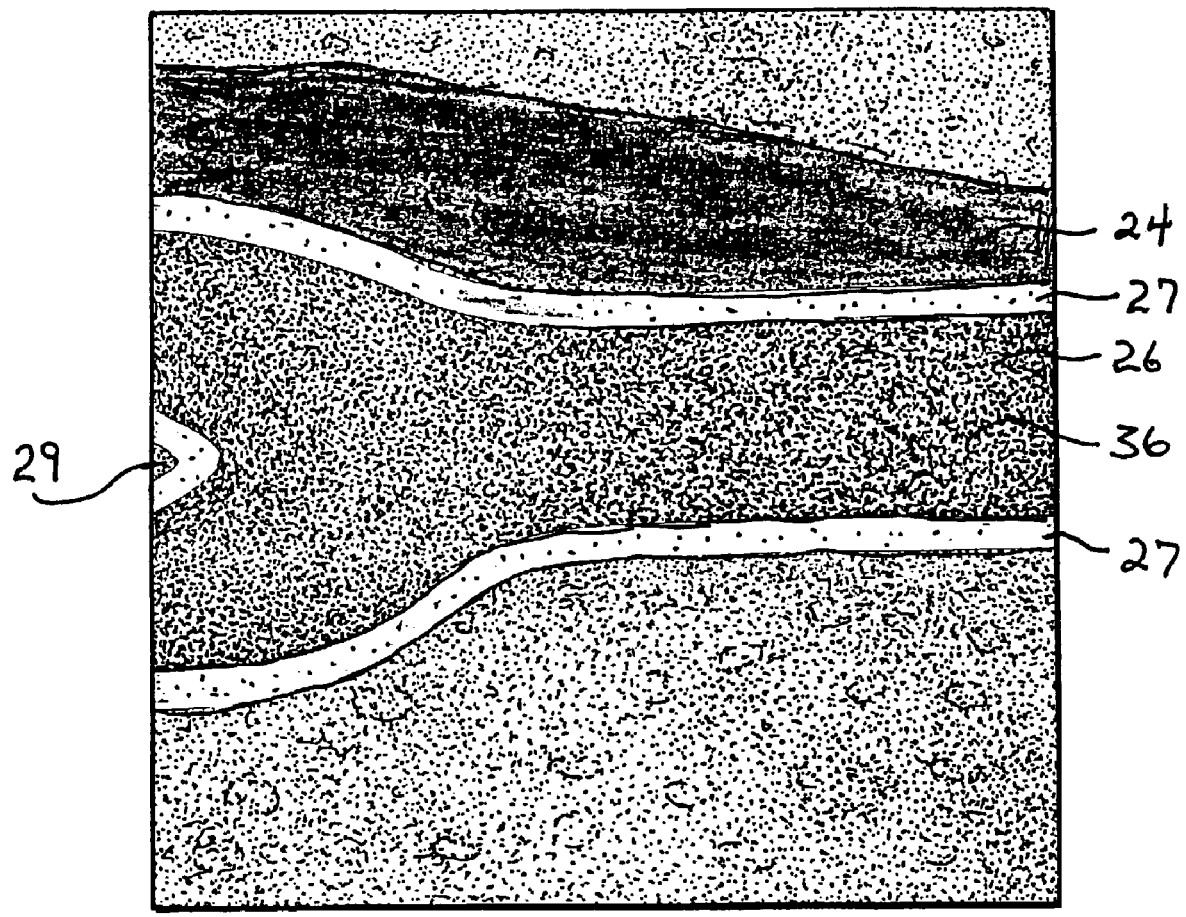
FIG. 3A is a simplified illustration of a longitudinal view of the right jugular vein stacked above the right common carotid artery and bulb, following transducer rotation in accordance with practice of the present invention.
Figure 3B:
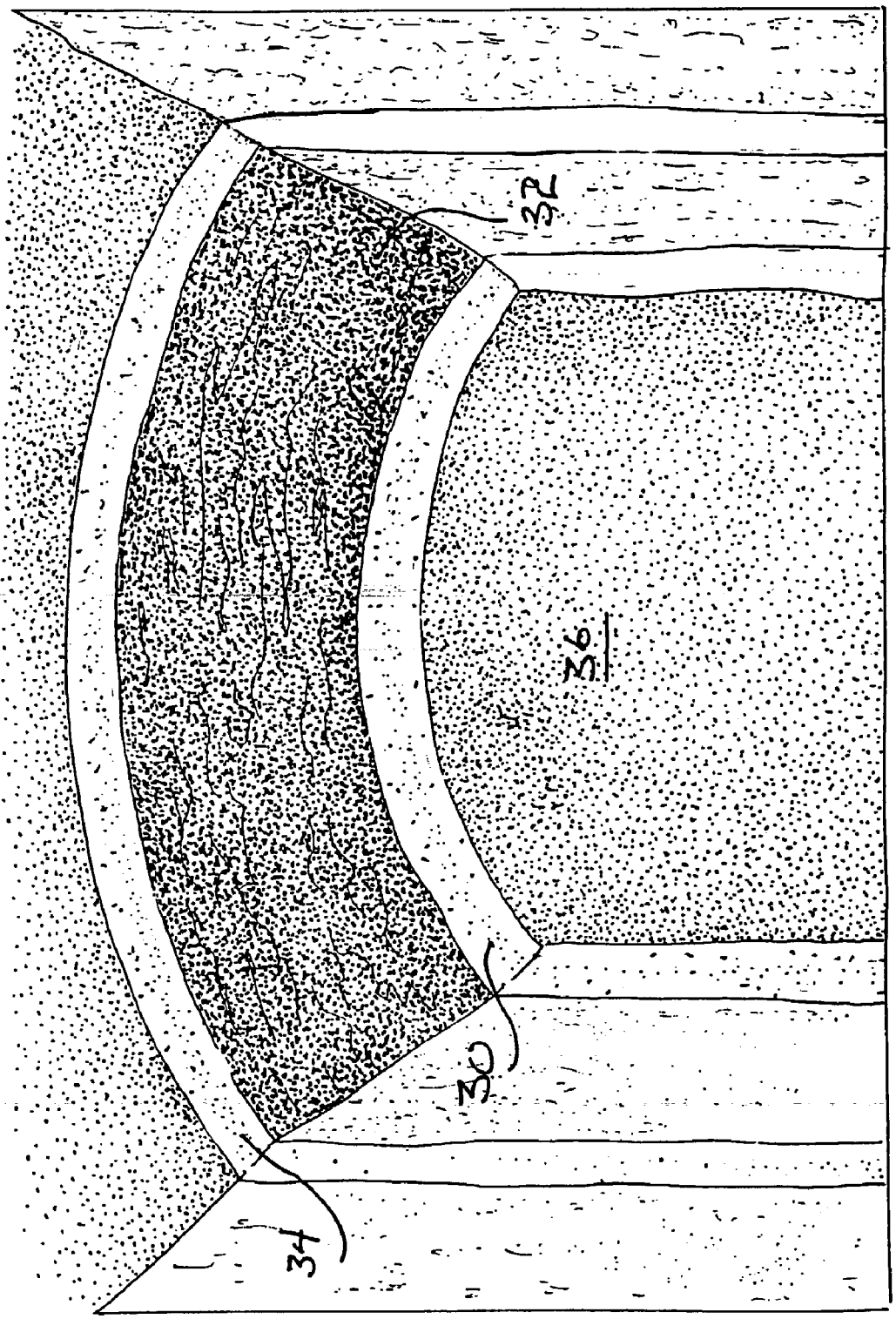
FIG. 3B is a simplified illustration of carotid arterial wall detail, including the intima-media complex.

In the exemplary illustration of FIG. 3A, and with regard to the arterial wall detail illustration of FIG. 3B, it will be understood that the longitudinal image is positioned along the carotid so as to contain anatomical landmarks for reproducing probe angulation, including stacking of the jugular vein 24 above the carotid artery 26 and visualization of the carotid bulb 18. An experienced operator will recognize the shape of the carotid bulb 18 and anatomy of the jugular vein and carotid artery and so position the image so as to expose an approximately 2 centimeter long region of the common carotid artery below the inception of the bulb along with juxtaposition of the jugular vein. Visualization of the region where the common carotid artery divides into the interior and exterior carotid arteries, termed carotid artery bifurcation 29, is also helpful in reproducing image position.

In this regard, and with particular attention to FIG. 3B, it will be understood that all arteries are generally formed of three distinct layers, an intima, media and adventitia, but the proportion and structure of each varies with the size, type and function of the particular artery. The innermost layer, the intima 30, suitably comprises a layer of endothelial cells which is characteristically thin in a young normal vessel, but which becomes thickened with age and other causes of atherosclerosis (e.g., genetics, lipid dyscrasias, smoking, hypertension, and other risk factors for vascular disease, atherosclerosis and cardiovascular disease). The middle layer, the media 32, contains smooth muscle cells. The media also suitably contains layers of elastic lamellae that alternate with layers of smooth muscle cells in elastic arteries, but with smooth muscle cells dominating in muscular arteries. The outer layer, the adventitia 34, typically contains loose connective tissue, nerves, small blood vessels and smooth muscle cells, particularly in large veins. A histological feature of larger arteries is the presence of longitudinally arranged smooth muscle cells in this layer.

In terms of ultrasound images, the individual layers comprising an exemplary common carotid artery wall are not independently visualized. Indeed, ultrasound reflections are generated at the interface between the blood lumen 36 and the intima layer 30, as well as the interface between the media 32 and adventitia 34. Thus, ultrasound images allow visualization of a region corresponding to the intima-media combination; thus, the term intima-media thickness (IMT), also referred to as the intima-media complex.

Figure 5:
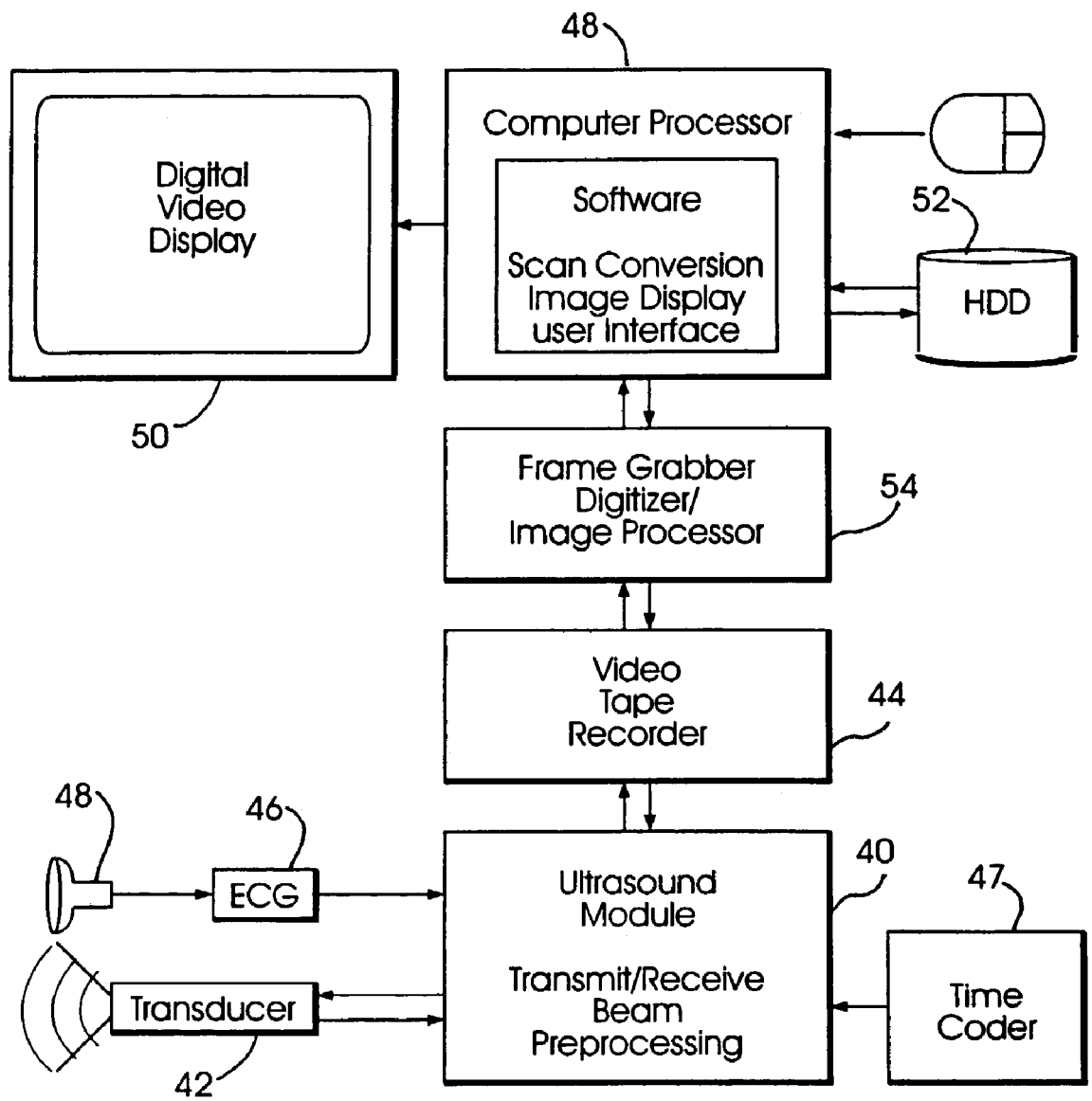
FIG. 5 is a semi-schematic, block-level diagram of an ultrasonographic carotid artery image acquisition and measurement system for standardized image acquisition for standardized arterial dimension measurements, in accordance with the present invention.

IMT measurements are made from the deep (or far) wall of the artery farthest from the skin starting in a region approximately 0.5 centimeters distal to the carotid bulb along a 1 centimeter length, using a standardized, computer generated "lock-out" ruler, away from the carotid bulb along the common carotid artery, and reflect a thickness of the intima-media complex defined by the near ultrasound reflection from the lumen-intima interface, and the far ultrasound reflection from the media-adventitia interface. Images are acquired by performing an ultrasound scanning procedure with an ultrasound system depicted in the exemplary embodiment of FIG. 5. In FIG. 5, a conventional, high resolution ultrasound apparatus 40 is coupled to a high frequency transducer 42 which is typically configured as a small part, vascular transducer. The transducer is conventionally a 7.5 to 10 MHz linear array transducer, and is coupled to any one of a series of commercially available ultrasound imaging systems. Exemplary systems include the ATL Ultramark IV, manufactured by ATL of Bothell, Wash., Toshiba SSH 140A ultrasound system, or other generally similar apparatus operating in B-mode. Images obtained by the ultrasound system 40 and transducer 42 are recorded on a video cassette recorder (VCR) 44 so as to be available for subsequent review. Additionally, an electrocardiograph (ECG) 46 is coupled to the system so as to provide an ECG signal from the patient that is recorded simultaneously with image acquisition and a trace of the ECG signal is superimposed on the ultrasound image. In conventional fashion, the ECG 46 receives a signal from conventionally placed electrodes 48 affixed to the patient's body in conventional fashion. Additionally, a time coder 47, counting in 100 ms intervals is coupled to the ultrasound system so as to provide a time code (time stamp or time reference) on each ultrasound frame. Each image frame is given an identifiable code used to locate individual frames or sets of frames for efficient retrieval.

Images acquired by the ultrasound system 40 are directed to a computer processing system 48 for acquired image display and analysis. Computer processing system 48 is contemplated as comprising a personal computer system (PC) including a graphic split-screen display monitor 50 and further including a non-volatile mass storage unit 52 such as a hard disk drive, JAZ drive, or a readable/writable CD ROM. It should be noted that there are very little processing constraints placed on the computer processing system 48. Indeed, a personal computer system utilizing an Intel 386-type processor and operating at speeds less than 100 MHz is certainly sufficient for practice of principles of the present invention. Those having skill in the art will understand that a more capable and faster computer system will be able to practice aspects of the invention with a greater degree of efficiency and speed, but raw processing power is not strictly required for the system to function quite adequately.

Prior to image analysis, a video image of the carotid artery is converted into a 512×480 pixel digital array, with 256 grey levels per picture element. Digitization is accomplished with an Epix PIXCI-SV4 or similar digitizing and image processing board 54 coupled to the computer processing system 48 through an internal bus, for example. The digitizing/image processing board 54 allows digitization of all images received either directly from the ultrasound system 40, or through playback of the VCR 44. Thus, images shown on the computer system's graphic split-screen display 50 are all digitized into a 512×480 pixel format.

The video signals from ultrasound systems are formatted to match the standards established for each region. In North America, the standard is 30 frames per second with 480 visible lines per frame. Each line is digitized into 512 picture elements (pixels) so that the digitized image size is 512 by 480 pixels. The European standard in most areas is 50 frames per second with 512 visible lines per frame. In this case, the digitized image is 512 by 512 pixels. The number of lines per frame is fixed by the video standard but the number of digitized pixels per line can be more or less than 512. This number was selected to allow two images to be displayed side-by-side on a commonly used 1024 by 768 computer split-screen display. A higher resolution computer display could be used but the size of the displayed image becomes smaller and more difficult to see.

Notwithstanding the foregoing, the display format is also chosen because of certain peculiarities pertaining to certain video cassette recorders. For example, a Sony VO 9500 MD VCR contains a digital memory that allows the computer to digitize a full 480 line video frame with the VCR in still mode. However, VCRs without frame memory, display only half-frame fields (240 lines) in still mode. Since accurate frame selection for IMT measurements requires the use of VCR still mode display, frame memory is a desirable feature in order to obtain full image resolution in the digitized image. Images are digitized to full frame resolution when the VCR is in normal play mode, but frame selection is a difficult process with the tape moving at normal playback speed.

Further, although the Sony VO 9500 MD VCR includes a digital frame memory, the digital data are not directly accessible to the computer processing system. In this particular example, the only VCR output is an analog signal, derived from the frame buffer and, as a result, a digitizing board is required in the computer system.

Figure 6:
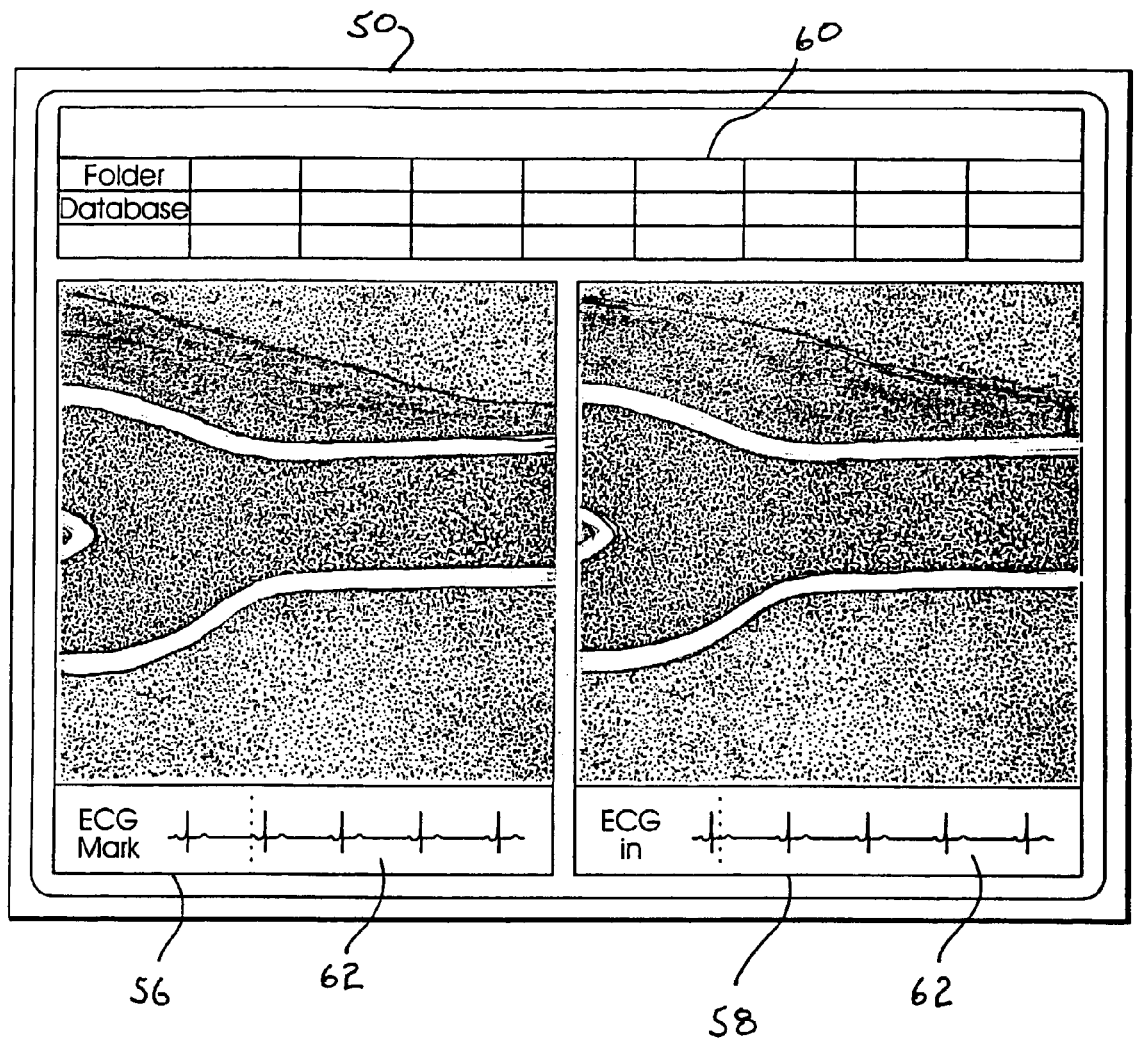
FIG. 6 is a simplified representation of a screen shot depicting one embodiment of a split-screen display system implemented for vascular image acquisition and vascular measurements such as arterial dimensions and intima-media thickness (IMT) in accordance with the present invention.

The process of digitizing the video ultrasound image, tracking the lumen-intima and media adventitia echoes, and computing IMT and arterial dimensions is accomplished with an application software program running on the computer processing system 48. Operation of this application software routine will now be described in connection with the exemplary screen shot depicting a split-screen implementation of an IMT measurement system of FIG. 6, in combination with a simplified flow diagram of a carotid artery longitudinal view comparison procedure of FIG. 7. It should be apparent that while the application software program is described more in connection with measurement data processing, those operational portions that support split-screen image display are particularly useful in connection with the image acquisition process described above.

Briefly, the application software routine implements a methodology that assists an operator to repeatably acquire images in a standardized fashion and accurately replicate measurements on images that have been obtained over different, spaced-apart examinations. The methodology utilizes a split-screen display, in which an arterial ultrasound image from an earlier examination is displayed on one side 56, for example, of a split-screen display 50, while a current ultrasound image from the current examination is displayed on the other side 58 of the split-screen display. By viewing both images, while manually adjusting the ultrasound transducer, an operator is able to find the real-time image that best matches the earlier image.

Specifically, the earlier arterial image 56 is one of several image frames that were chosen for analysis during a previous examination. Each frame was chosen for the clarity of the image produced, and the quality of the IMT (i.e., well-defined boundary echoes with a minimum of voids and discontinuities). These images were processed and IMT measurements and vascular dimensions taken therefrom, in a manner to be described in greater detail below, with all of the data pertaining to each frame stored in a file or set of files in non-volatile mass storage memory (52 of FIG. 5) or on a JAZ Drive or CD ROM identified to a particular patient. A menu bar 60 is disposed along the top of the split-screen display 50 and comprises a set of selectable tasks from which the application software routine is operable. Such tasks necessarily include "get file" so that an operator is able to select and extract previous images for a particular patient, by accessing their file data and uploading the information contained therein. As described above, images contained within the file are displayed on the left-hand side of a split-screen display 56. Additional menu items might include commands to "advance" which, when selected, might advance from one frame to another within the selected file, displaying each frame in the left-hand screen portion 56.

As presently contemplated, there are approximately 25–30 commands disposed within the menu area 60 which represent the most frequently used commands made to the program. Additional pull-down menus contain further commands less frequently used. Frequent commands include "Record Dir," which displays records in a selected database file, "Store New" which stores a selected record as a new record, and "Replace Rec" which replaces a stored database record with a current selected record. "Set Tracking" is used to select if arterial diameter or IMT is to be measured and to set other properties of the tracking display. Other commands, such as "Show Pts", allow an operator to display previously selected manual tracking markers and "Fix Pts" allows an operator to adjust manual tracking markers, as will be described in greater detail below. Further, "Zoom/Unzoom" allows an operator to zoom an image by various multiplication factors and "Step Frame" allows the operator to step through a database record-by-record in order to apply corrections if necessary.

A "Digitize" command puts the frame grabber (digitizing and image processing board) into a continuous digitized/display mode. Mouse access (by right clicking, for example) terminates the sequence, in effect freezing the image. All newly digitized images are temporarily identified with a temporary file name, such as digit.dmp until the image is given a permanent name with the command "Name Image". An "Image Right" command displays the current image to be processed on the right side of the split-screen display 58, which is the screen portion where tracking and measurement functions are operative. An "Image Left" command is used to position a reference image on the left side 56 of the split-screen display 50. As an example, an image from a prior ultrasound examination is stored in an active folder and a matching image is located from a current ultrasound examination from a videotape or from a direct feed from an ultrasound transducer. The image from the prior examination is placed on the left side of the split-screen display while the "Digitize" command implements real-time images from the videotape or transducer on the right side of the screen for comparison. Further tracking, calibration and measurement commands will be discussed in more detail below, during that part of the software operation regime that pertains to image processing for IMT and arterial dimension measurements.

Figure 4:
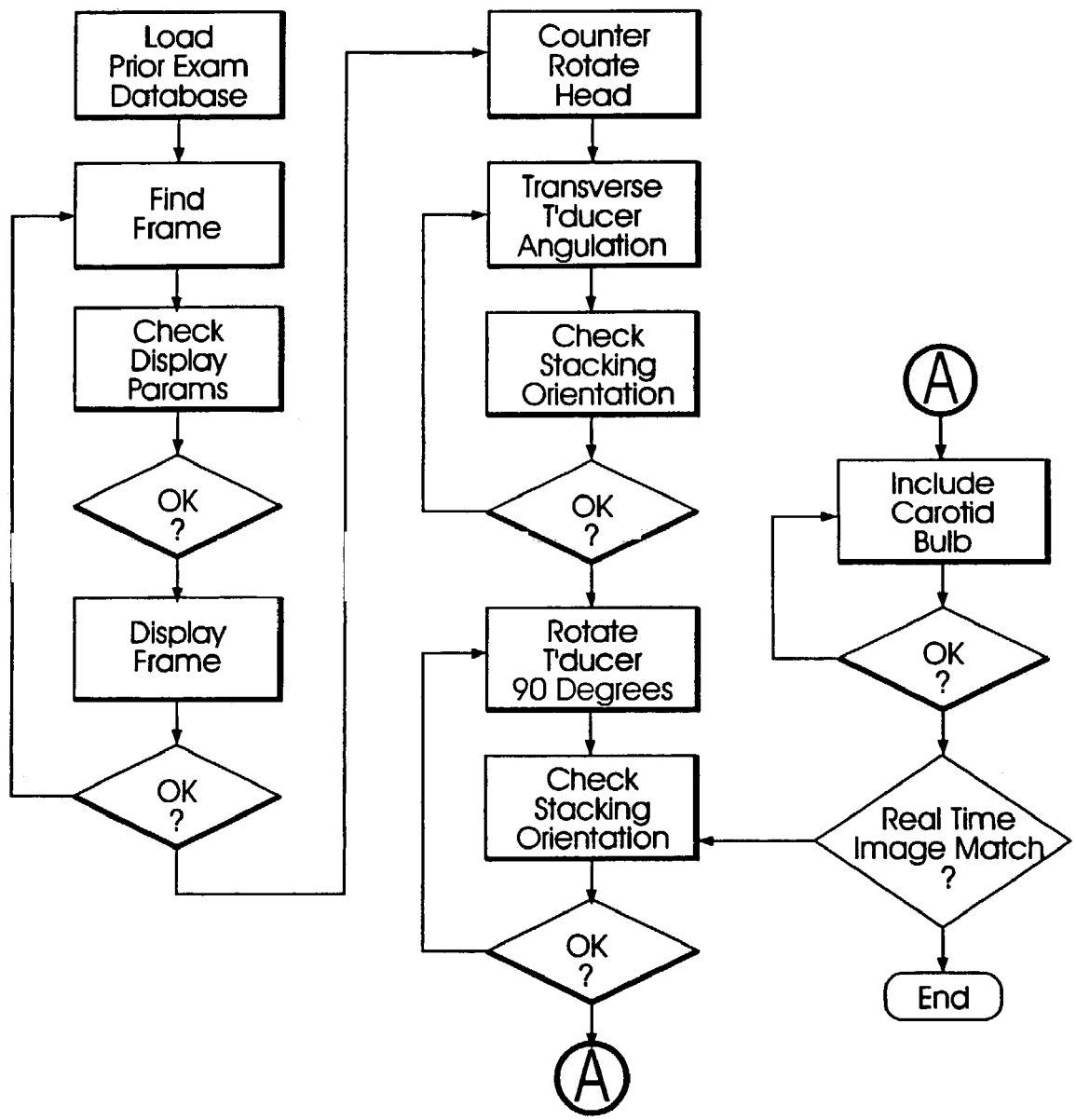
FIG. 4 is a simplified block-level flow diagram of an ultrasonographic examination procedure in accordance with practice of the present invention.
Figure 7:
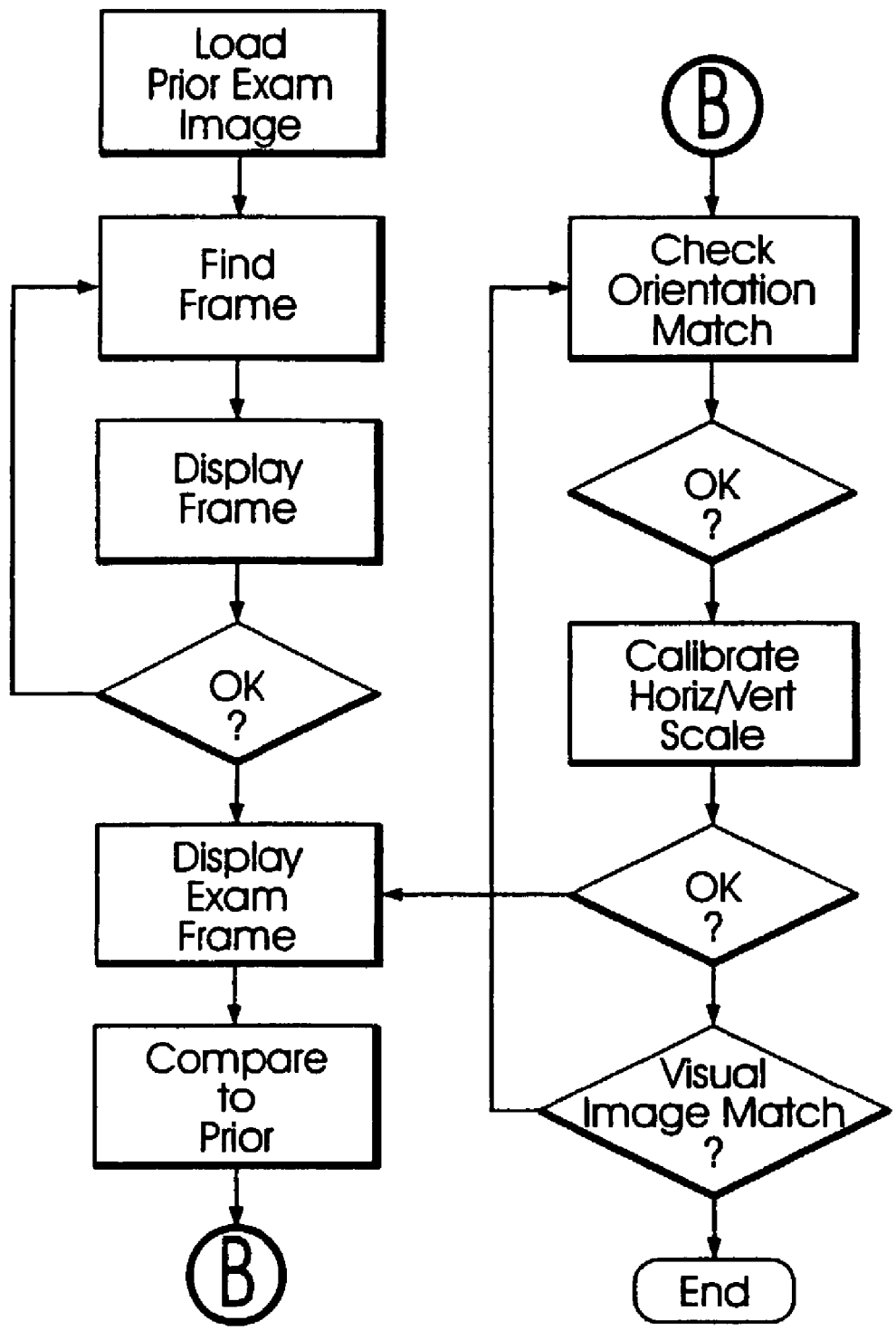
FIG. 7 is a simplified flow diagram of a carotid artery view comparison procedure in accordance with the invention.

In accordance with the exemplary image acquisition procedural flow diagram of FIG. 4, and the exemplary measurement preparation procedural flow diagram of FIG. 7, prior ultrasound examination images are displayed on the left side 56 of the split-screen display 50 in order that an operator is able to evaluate positioning of the transducer so as to obtain a present image that corresponds to the previously stored image in as great a degree as possible. The particular shape, aspect and general appearance of the previous image serves as a visual reference to the operator in order to obtain as exact a replication as possible. During image acquisition, minute adjustments in transducer probe position and angulation are made until such time as the real-time present image 58 closely matches all of the parameters of the stored image 56. In this regard, for each individual and for each examination, the depth of field, gain, monitor intensity setting, and all other initial instrumentation settings used for a baseline examination, are recorded for each set of images contained in any one database and are maintained therein for all follow-up examinations. Although, a hard copy of each individual's baseline image might be used as a guide to match a repeat image to a baseline image, the split-screen methodology discussed in connection with FIGS. 4, 6 and 7 define a preferred direct visual aid methodology for reproducing probe angulation.

Image comparison and matching is also performed during a standardized measurement process, as depicted in FIG. 7. In particular, a set of images acquired in accordance with the standardized acquisition process described above during a prior examination is extractd from a "prior examination" database, and a suitable frame is displayed on one half of the split-screen display as a reference image. The displayed frame should correspond to a frame upon which IMT and/or vascular dimension measurements were made during the prior examination. Current examination ultrasound frames are displayed on the other half of the split-screen display and evaluated against the reference frame in order to find the best match. The visual reference structures used to acquire the images also function to support a more reproducible match between images obtained and measured during the prior examination and those being evaluated for measurement during the current examination. Image matching during the measurement as well as the acquisition procedures reduces measurement variability and substantially improves the repeatability of arterial dimension measurements, thereby allowing effective long-term trend analysis.

As a further aid to reducing measurement variability, an ECG recording is displayed along a bottom portion 62 of the split-screen display, as well as time code information displayed in a top corner, in a manner that allows image frames to be selected based on their occurrence within a particular cardiac cycle (i.e., such that the same phase of the cardiac cycle is examined for all IMT and vascular dimension measurements). By way of an additional example, arterial diameter measurements need to be made at the times of maximum and minimum internal pressure, such that elasticity values may be obtained from maximum and minimum internal diameter measurements. It is well understood by those having skill in the art that maximum and minimum internal pressures have a direct relationship to the occurrence of a measurement with regard to the timing of the P-wave and R-wave.

Further, and in accordance with the invention, the greatest degree of accuracy and reproducibility is obtained when IMT measurements are made during the minima of arterial excursions (lowest carotid arterial distending pressure) which occurs in the ECG tracing between the P-wave and the R-wave. Thus, for each ultrasound examination, matching longitudinal views of the common carotid artery are located and approximately 80 successive frames, representing a minimum of two cardiac cycles, are digitized. The number of frames chosen is not particularly relevant to practice of the invention, since with conventional computer systems, 80 or more frames can be acquired and stored on a high speed hard disk drive in real-time from a single VCR pass. All that is necessary in the context of the invention is that a number of image frames be taken over at least two cardiac cycles, such that at least two to three frames will occur at any given portion of the cardiac cycle. Thus, an operator is assured of obtaining at least one frame per cycle that is properly positioned in the minima between the occurrence of the P-wave and R-wave of the ECG trace. Once these images are acquired and stored, the operator is able to recall the stored frames and once again compare them to the reference image located on the left side 56 of the split-screen display 50.

Whether viewing a current image or a recalled image on one side of the screen 58, the operator must ensure that the active image matches the reference image as closely as possible, not only in aspect and positioning, but also in the quality of the intima-media region and the reflection of the boundary edges. Additionally, the operator must ensure matching of all of the anatomical references, such as the jugular vein, carotid bulb, etc, and the ECG phase (the p-wave, for example). With regard to reflection boundary quality, the lumen-intima and media-adventitia ultrasound echoes are optimally visualized when the ultrasound scan is perpendicular to the vessel walls. The transducer probe is positioned to maximize the brightness of the intima-media complex echo and minimize gaps in the echo. When the ultrasound beam is approximately perpendicular to the vessel wall, the reflected signal from the intima-media complex is maximized and produces the brightest signal. Similarly, the intima-media complex echo has the fewest gaps when the ultrasound beam is perpendicular to the vessel wall. Accordingly, it will be understood that the initial patient placement, transducer probe manipulation so as to obtain a visualization of jugular/carotid stacking, in the transverse view, and probe rotation about the stacked central image line axis to obtain visualization of jugular/carotid stacking in the longitudinal view, all function in combination to provide a standardized methodology by which image quality and reproducibility are ensured, thereby enhancing valid image matching.

In order to refine image matching, both the right and left side images must be displayed on the split-screen system in accordance with a corresponding scale. In other words, the application routine must know the spacing in millimeters represented by adjacent picture elements (pixels) in both the horizontal and vertical direction, for each image. A "calibration" command is selected from the menu box 60 and for each calibration, vertical and horizontal, two points are identified whose real separation in millimeters is known. The operator is requested to identify each of two reference points, by cursor selection (mouse click, or the like) and then enter the known separation of the reference points in millimeters. In this regard, many ultrasound systems employ some form of reference grid marks in the vertical and/or horizontal direction in five or ten millimeter intervals, and these are of great utility in performing the calibration procedure. However, although these reference grids are helpful, care must be taken to validate the reference intervals. Generally, the greatest accuracy is obtained by identifying and selecting reference marks which are separated as far as possible. The process is repeated for both horizontal and vertical calibration and "pixel spacing horizontal" and "pixel spacing vertical" are saved for each image. Pixel spacing values for one image are normalized to the values obtained for the other, such that both images are displayed with respect to a unitary system of pixel spacing.

Once the image of the present ultrasound examination is matched to the image of a previous ultrasound examination, a number of frames are acquired from the present ultrasound examination sonogram, as described above, and stored in non-volatile memory for further processing. All of the instrumentation settings are captured and stored, along with the image, in a particular database associated with that specific patient. Time stamping and time coding are used so that each image, or set of images, is associated to a particular examination date, such that long-term evaluations of the mechanical and structural properties of the arterial wall may be precisely undertaken. The recently acquired images are analyzed by the software application program, in accordance with the invention, in order to track the near and far wall media-adventitia or lumen-intima echoes in order to derive arterial diameter over an approximately 1 centimeter length of the common carotid artery at a standardized location starting approximately 0.5 centimeters distal to the carotid artery bulb. Additionally, the far wall lumen-intima echo, tracked over the same segment, is used together with the far wall media-adventitia echo to determine IMT. Arterial diameter and IMT, for each frame, are taken as the respective average of approximately 70–100 individual measurements of diameter and IMT acquired along the 1 centimeter segment (assuming there are 70–100 matched pixel pairs per centimeter).

In general, when a single frame is analyzed by the system, an operator uses cursor control to identify several points along each echo boundary (lumen-intima echo and media-adventitia echo). A smooth curve generated through these identified points, serves as a guide to an edge detection process, where the system searches in the vicinity of the generated curve for the true boundary, using an intensity gradient detection method to be described in greater detail below.

When multi-frame detection is required, only the first frame of a multi-frame sequence is processed in the above-described fashion. The second and additional frames reuses the true detected edge coordinates from the first frame as an approximation to the boundary curve for the edge detection process of the next frame. The true boundary of the second frame is used as an approximation for the third frame edge detection process, with the sequence being repeated until all frames have been detected. Operator intervention is only required when there is a discontinuity between frames, such that the artery moves a relatively large distance between frames and causes the automated edge tracking methodology to fail. This effect is most frequently seen during the systolic expansion of the artery, in which case the operator redirects the tracking routine to the general vicinity of the changed boundaries.

Once appropriate boundary conditions are obtained, maximum and minimum arterial diameters, and the IMT at the point of maximum diameter and minimum diameter are determined over each cardiac cycle. Arterial dimensions (IMT and diameter) are averaged over two successive cardiac cycles and the arterial diameter and IMT values are used, together with blood pressure measurements, to calculate several standard arterial stiffness indices (elasticity and compliance measurements).

Figure 12:
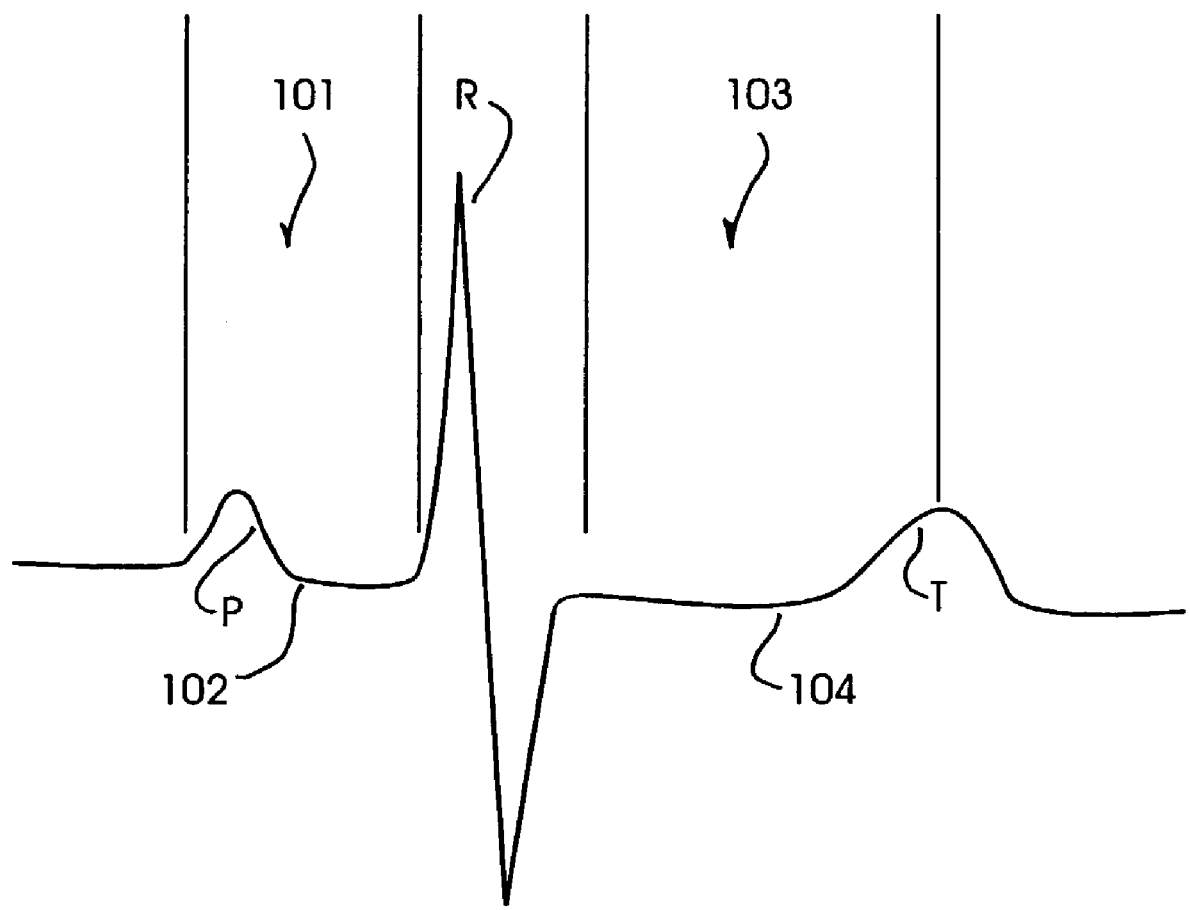
FIG. 12 is a simplified graphical representation of an ECG trace illustrating the approximate positions of the P-wave and R-wave.

Further, IMT measurements are obtained at the point of minimum and maximum arterial diameter in order to compare the difference in IMT during minimum and maximum arterial excursion. This is roughly equivalent to end-diastole and peak systole, respectively. It has been empirically determined that the point of minimum arterial diameter occurs approximately in the interval region 101 between the P-wave and the R-wave, and more particularly, in the region just at the end of the P-wave, as depicted generally at 102 in FIG. 12. Similarly, maximum arterial diameter occurs at a point, indicated generally at 104, in the interval 103 between the end of the R-wave and the peak of the T-wave. Given the image acquisition methodology of the present invention, there are approximately two (on average) video frames occurring in the interval from the beginning of the P-wave to the minimum diameter point, as well as the interval from the minimum diameter point to the beginning of the R-wave and from the maximum diameter point to the peak of the T-wave. There are approximately six (on average) video frames occurring in the interval from the beginning of the R-wave to the maximum diameter point. Thus, it will be understood that capturing a suitable number of frames over two complete cardiac cycles will almost always give one frame occurring at the requisite points, i.e., minimum arterial diameter and maximum arterial diameter.

A particularly advantageous feature of the invention allows for increased measurement accuracy by averaging measurement results obtained from two frames of information. This feature evaluates measurement data from sequential frames occurring in the ECG trace intervals and thereby minimizes variability resulting from location along the trace. Two frame averaging, in a manner similar to that described above, utilizes the respective average of approximately 70–100 individual measurements of diameter and IMT acquired along the standard 1 centimeter length of each frame. Additionally, two frame averaging may be performed on two frames that occur at substantially the same time, with respect to the ECG trace, but during consecutive cardiac cycles. Frame averaging is thus useful in reducing inter-cycle variability as well as intra-cycle variability.

Figure 9:
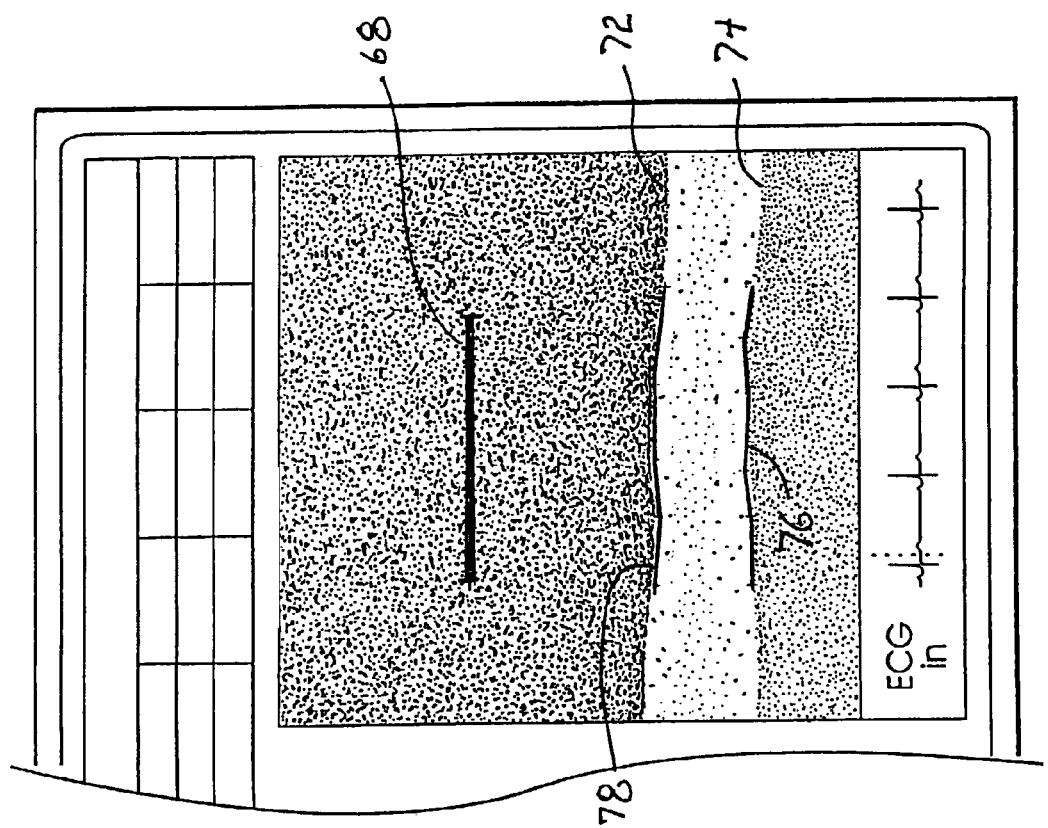
FIG. 9 is a simplified representational screen shot depicting the selected frame of FIG. 8, illustrating a best fit curve generated through the boundary markers.
Figure 8:
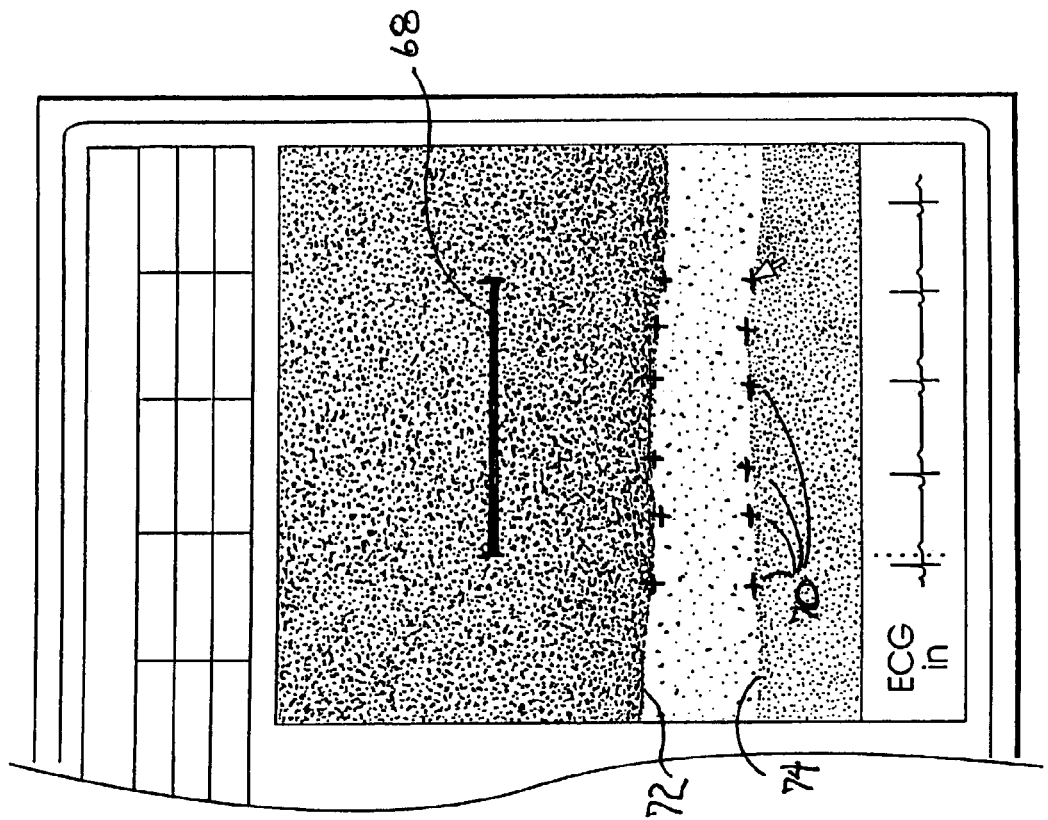
FIG. 8 is a simplified representational screen shot of one side of the split screen display of FIG. 6, depicting a zoomed-in view of a selected ultrasound frame, illustrating boundary marker placement.
Figure 10:
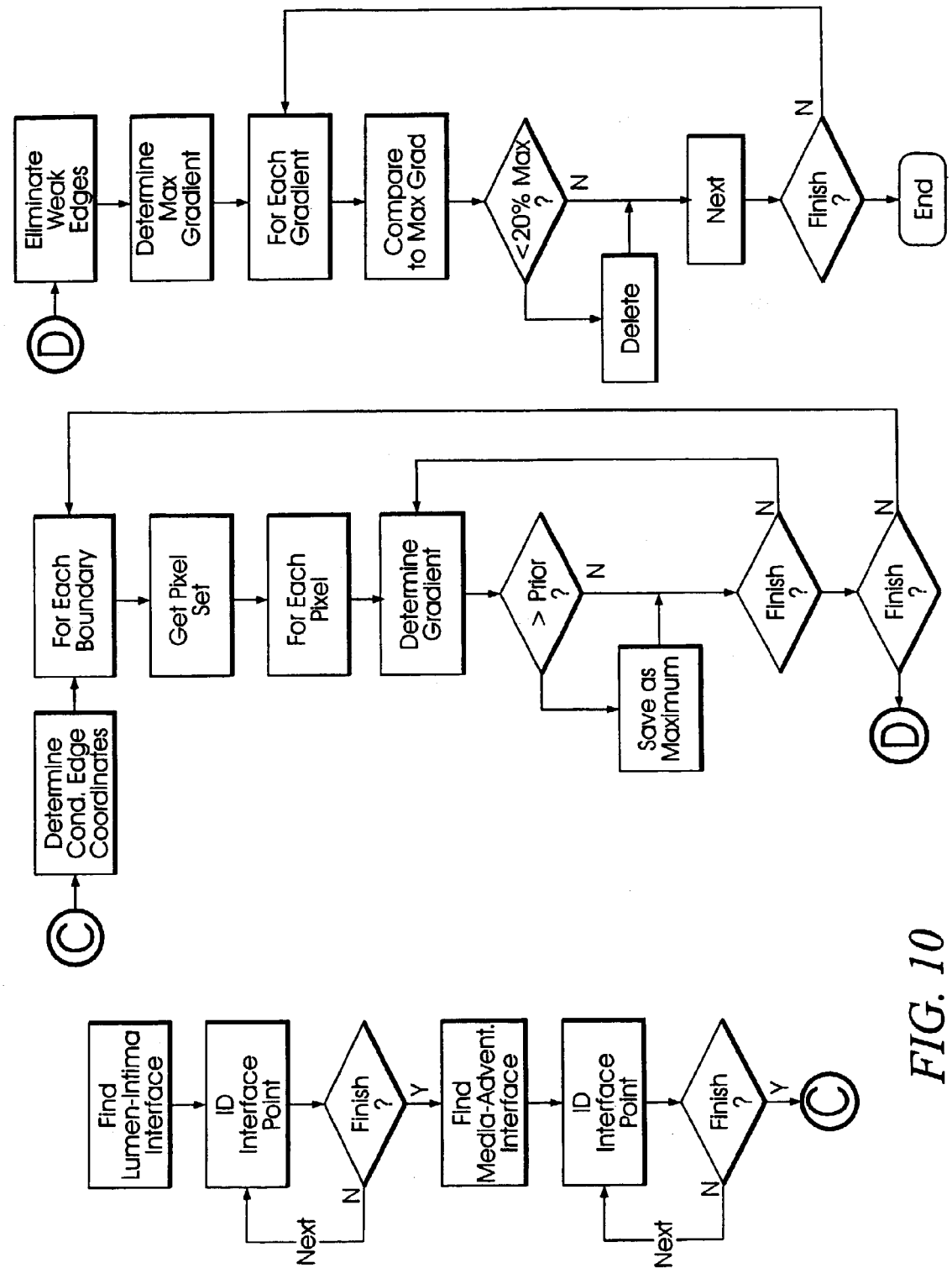
FIG. 10 is a flow diagram of one embodiment of an intima-media thickness (IMT) determination methodology.

The lumen-intima and media-adventitia echoes are located in accordance with a three-step methodology that will now be described in connection with the exemplary screen shots of FIGS. 8 and 9 and the flow diagram of an IMT measurement methodology of FIG. 10. Initially, a selected frame is displayed on the operative (tracking) portion of the computer processing system's split-screen display (50 of FIG. 6) and a calibration procedure is performed, such that the image size is correlated to pixel data, as previously described. The image may be expanded in order to zoom-in on an appropriate region of the arterial far wall and the lumen-intima and media-adventitia echoes visually confirmed. An approximate echo boundary is identified and delineated for both the lumen-intima and media-adventitia boundaries by a series of cursor-placed boundary markers. The approximate boundary for each echo is used to guide an automated edge finding algorithm in order to locate an initial or "conditional first-pass" set of edges. A second set of approximate markers are derived from the first-pass edges by using the row coordinate of the first-pass edge row coordinates that correspond to each column of the initial markers. The sequence of fitting a smooth curve through the new markers and using this new approximate boundary as a guide for edges, is repeated. The second-pass computer-defined edges are then tested for "edge strength" and false or weak edges are eliminated. It should be noted that initial manual placement of boundary markers functions only to narrow the boundary search parameters for the system. Actual boundary definition and subsequent measurements performed with respect to the defined boundaries are performed automatically by the system. Accordingly, human measurement error is virtually eliminated.

In determining an approximate echo boundary, cursor boundary markers are placed at the leading edge of the echo at a few points, within a 1 centimeter horizontal range. In order to standardize the 1 centimeter range, a 1 centimeter scale 68 is superimposed over the image in order to define the region in which cursor points will be considered value, as illustrated in the exemplary embodiment of FIG. 8. The scale 68 is computer generated and functions as a "lock out" scale by defining a horizontal region within which boundary markers may be placed for measurement. Only those markers disposed within the 1 centimeter horizontal range delineated by the "lock out" scale will be recognized by the system for further processing. Those markers outside the range of the scale will be ignored. Manual boundary markers, indicated generally at 70, are placed on both the lumen-intima and media-adventitia echo leading edges, 72 and 74 respectively, with the cursor boundary markers being a different color for each edge, in order to provide a visual aid to the operator during the approximation process. In the event a particular cursor marker is misplaced, an operator may right-click, for example, on the marker thereby deleting it and then left-clicking in order to place the marker in a more advantageous position. Following cursor placement at both interface edges, and with reference to the exemplary embodiment of FIG. 9, the operator accesses a "curve fit" command by which the system generates a smooth continuous curve, for both the lumen-intima 76 and media-adventitia 78 edges which conforms to and includes each of the cursor-placed boundary markers.

Next, the system searches for edges in a direction perpendicular to the approximate boundary defined by the smooth continuous curve fit to the corresponding set of boundary markers. At each point (defined by each pixel along the horizontal) of the approximate boundary, 13 pixels of the image are automatically examined that lie along a line perpendicular to the boundary. The system automatically selects half of the examined pixels from one side of the approximate boundary and half from the other, with the central pixel chosen as the one comprising the approximate boundary itself. Since the approximate boundary is selected to coincide visually with the leading edge of the echo, coordinates of the "true" boundary edges typically fall within three to four pixels of the approximate boundary.

Figure 11B:
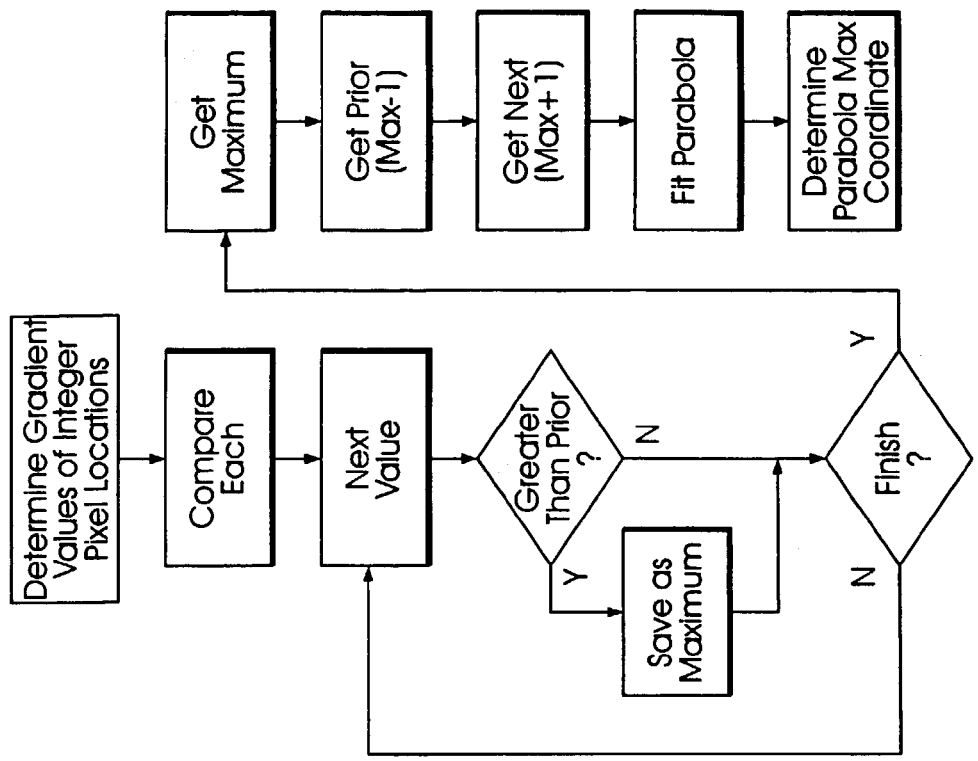
FIG. 11B is a simplified flow chart of one embodiment of a maximum gradient calculation procedure.
Figure 11A:
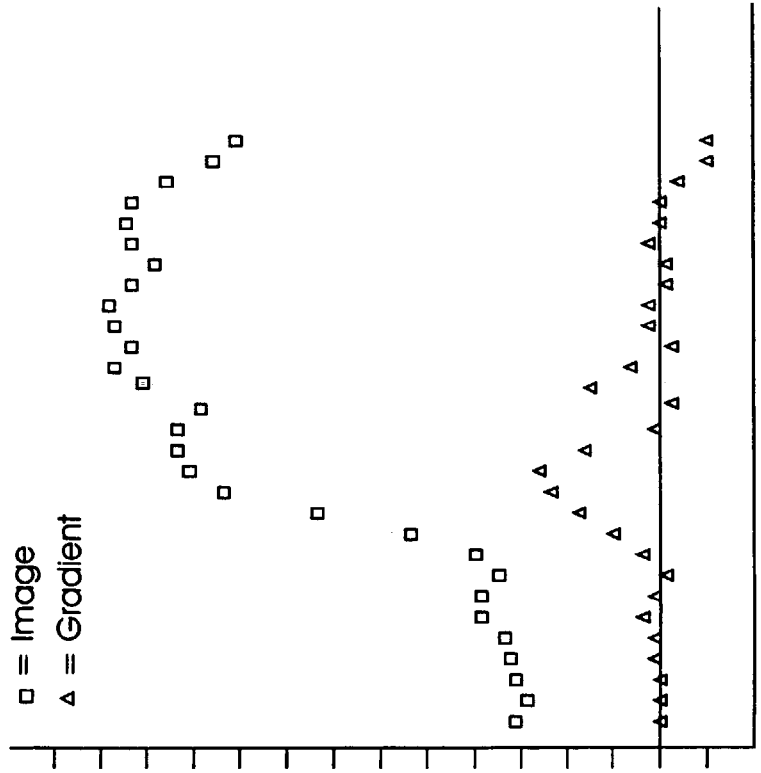
FIG. 11A is a graphical representation of image intensity and computed intensity gradient, along one sample edge.

The system-determined echo boundary is defined as that point within the 13 pixel sequence at which the rate of intensity change (or intensity gradient) of the pixels is at a maximum. Specifically, the rate of change of intensity, at a particular pixel in the sequence, is computed as the derivative of a second degree polynomial fit to the five pixels centered on the pixel in question. The process is iterative, and repeats for each of the pixels, beginning with the third and ending with the eleventh. An exemplary graph of image intensity values and computed gradient at one point of an exemplary lumen-intima echo is depicted in FIG. 11A.

The integer location in the image of the pixel with the largest gradient is initially taken as the echo boundary, but, as discussed in greater detail below, the maximum gradient of the pixel sequence can often occur between pixels. Further, edges determined to sub-pixel resolution are considerably more accurate than edges determined to an integer pixel resolution. For example, and with regard to sub-pixel edge detection resolution, two identical maximum gradient values might be obtained for two adjacent pixels. In this particular situation, the maximum gradient for the sequence might be selected as the point mid-way between the two pixels.

In order to determine a sub-pixel maximum gradient location, the nine gradient values, corresponding to integer pixels three through eleven, are determined in the manner as described above, and the resulting values are compared to determine the largest value. A parabola is fitted to the three gradient values centered on the largest value and the coordinate of the parabola maximum is taken as defining the sub-pixel edge location.

The coordinates of edge points determined by the maximum gradient location procedure are labeled as conditional edge points and are converted to true edge points, or discarded, based on gradient value uniformity calculations. After conditional edges are determined for all points (each pixel along the 1 centimeter horizontal distance), the gradient value for each pixel along the conditional edge is compared with the maximum gradient value found for all the points along the conditional edges of that particular echo. Conditional edge points having gradient values less than 20% of the maximum value are considered "weak" edge points and are subsequently deleted, with the remaining edge points deemed acceptable. This procedure minimizes identification of spurious edge points due to image noise, voids, defects, or other perturbations in the arterial wall image. The 20% value is arbitrary, but was chosen because of certain image generation characteristics of particular ultrasound scanner apparatus. For a range of carotid images obtained with certain ultrasound systems, spurious edges often tend to be accepted when the deletion threshold is set at a value lower than about 20%, and valid low intensity edges tend to be rejected when the deletion threshold is set at a higher value. The 20% threshold value is considered suitable for use in connection with images generated from the majority of ultrasound apparatus in common use. Naturally, as ultrasound imaging technology improves, the rejection threshold may be further refined through simple empirical test procedures, in order to further improve the accuracy of edge detection.

After the edge tracking process has been applied to the lumen-intima and the media-adventitia echoes, the distance between all acceptable edge point pairs along the 1 centimeter distance are measured, averaged, and the mean separation between all the acceptable edge point pairs computed as IMT. The process is repeated for the media-adventitia edge points and, for each acceptable media-adventitia edge point, a line is drawn that is locally perpendicular to the media-adventitia edge points and which intersects the lumen-intima boundary. Gaps in the lumen-intima boundary, due to deleted edge points, are temporarily filled by linear interpolation from the pixel coordinates of the nearest acceptable edge points, in order to define acceptable edge point pairs.

Where the lumen-intima edge point closest to this line is an original acceptable edge point (i.e., not an interpolated edge point), it is paired with the media-adventitia edge point and the distance between the pixel edge points is calculated to the nearest pixel. Where the nearest lumen-intima edge point is an interpolated edge point, the media-adventitia edge point under consideration is assumed not to have a matching edge point and the media-adventitia edge point is discarded and the process is repeated for the next media-adventitia edge point until all edge point pairs are either used for IMT distance calculations or discarded.

Average IMT is computed as the mean of the calculated distance between all acceptable edge point pairs. By way of example, IMT for an average adult will fall in a range of approximately 0.65 to 0.9 millimeters, with the average being approximately 0.75 millimeters. On average, acceptable matching edge points can be found for about 70% to about 80% of the potential edge point pairs of a standardized 1 centimeter portion of a typical arterial wall image.

With respect to arterial diameter measurements, it will be understood by those having skill in the art that the same methodology is applied to arterial near wall echoes as to the far wall echoes, with distances calculated between pixel pairs between the near and far wall lumen-intima boundaries, defined along a standardized 1 centimeter length.

The foregoing has been an exemplary description of a standardized protocol and system for the acquisition and processing of radio frequency ultrasound images of human vascular structure. An antero-lateral longitudinal view of the far wall of the right or left common carotid artery is obtained with the head disposed approximately 45° in the contralateral direction. The lumen-intima and media-adventitia echoes are optimally visualized when the scan lines are perpendicular to the arterial wall. The transducer is positioned in order to maximize the brightness of the far wall IMT echo and to minimize gaps in the echo. When the ultrasound beam is approximately perpendicular to the wall, the reflected signal from far wall IMT echo is maximized and produces the brightest signal. Similarly, the far wall IMT echo has the fewest gaps when the ultrasound beam is perpendicular to the vessel wall.

In order to so position the ultrasound beam and ensure repeatability of image acquisition and measurement on an examination-by-examination basis, an operator first acquires a reference image defined by a stacked structure comprising the jugular vein and carotid artery, with the jugular vein and carotid artery disposed in a specific relationship such that the ultrasound beam will be perpendicular to the vessel wall, as the transducer is rotated 90°.

The proximal portion of the carotid bulb is included in the image for reference purposes to allow for image matching and standardized measurements on an examination-by-examination basis. All images are captured using the lowest power and signal gain consistent with the visualization of the arterial wall echoes.

One end diastolic frame is selected from a 5–10 second recorded sequence, using maximum IMT continuity and maximum echo brightness as a selection criteria. Further, the selected frame is chosen from a number of suitable frames based upon a matching procedure carried out on a split-screen display, with present examination images shown on one half and prior examination images shown on the other. The frame with the best visual match and containing suitable continuity and brightness criteria is selected.

Average IMT is computed over a 1 centimeter length of the common carotid artery far wall beginning approximately 0.5 centimeters distal to the transition between the common carotid and bulb regions. This transition region is identifiable in most cases by a relatively abrupt change in the angle of the far wall at the beginning of the bulb. The longitudinal position of the analyzed segment is carefully matched to the longitudinal position of analyzed segments of that particular patient's prior examination, by again performing a split-screen display comparison of the present and prior images.

The foregoing description of systems, standardized protocols, algorithms and standardized procedures for improving and standardizing ultrasound image acquisition for replication for repeatable vascular characteristic measurements have been set forth in connection with certain exemplary embodiments which are intended only as illustrations of the present invention and are not intended to represent the only forms in which the present invention may be constructed and/or utilized. It will be evident to one having skill in the art, that major simplifications, modifications and enhancements may be made to the exemplary embodiments and the same or equivalent functionality may be accommodated without departing from the spirit and scope of the invention. For example, image resolution may be increased with improved ultrasound transducers. However, for applications in which IMT and vascular dimensions serve as a clinical trial end point, absolute accuracy of the IMT and vascular dimension measurements is not as important as the error in detecting IMT and vascular dimension change. The systems and standardized methods described above are certainly adequate for developing IMT measurements with an absolute error less than 5% to 8%. Accordingly, the present invention is intended to encompass the full scope and spirit of any structure, protocol or method that falls within the coverage of the appended claims.

What is claimed is:

1. A method for accurately replicating ultrasound images of vascular structure, taken at spaced-apart examination intervals, so as to develop a set of substantially congruent sequential images of the vascular structure, the method comprising:

orienting a patient position such that a first side of the neck is exposed and the head is counter-rotated about 45 degrees;

positioning an ultrasound transducer so as to develop a transverse image view through a neck section chosen to contain a visualization of a carotid artery and a jugular vein;

displaying the transverse view on a split-screen display;

manipulating transducer position and angulation until the jugular vein and carotid artery are displayed in a substantially vertical stack orientation, the stack defining an approximate vertical axis through a center of the jugular and a center of the carotid; and rotating the transducer through about 90 degrees around the approximate vertical axis, so as to develop a longitudinal image view along a length of the carotid artery, while maintaining the jugular vein and the carotid artery in the substantially stacked orientation.

2. The method according to claim 1, further comprising:

displaying the longitudinal image view of the carotid artery, in real-time, on a first half portion of a split-screen display;

retrieving a longitudinal image view along a length of the carotid artery taken during a previous ultrasound examination;

displaying the previous longitudinal image on a second half portion of the split-screen display; and further manipulating transducer position so as to bring the real-time longitudinal view into congruence with the retrieved longitudinal view by visual comparison of the images displayed in the first and second half portions of the split-screen display.

3. The method according to claim 2, wherein each longitudinal view includes anatomical landmarks for reproducing transducer angulation.

4. The method according to claim 3, wherein, the anatomical landmarks include the jugular vein and a portion of a carotid artery bulb structure, each longitudinal view further including an image of at least a length of a far wall portion of the carotid artery distal to the carotid artery bulb portion.

5. The method according to claim 4, further comprising:

retrieving a set of display characteristic parameters of ultrasound imaging instrumentation settings associated to the previous obtained longitudinal image; and replicating the ultrasound imaging instrumentation settings on the display for the real-time longitudinal image.

6. The method according to claim 5, further comprising:

acquiring an ECG trace in simultaneous fashion with the acquisition of the real-time longitudinal image, an ECG trace being acquired in substantially similar fashion for the retrieved previously obtained longitudinal image; and displaying the corresponding ECG trace with the respective longitudinal image, each ECG trace defining a time index such that real-time and previous longitudinal images are displayed at substantially the same time during a cardiac cycle.

7. The method according to claim 5, wherein the ultrasound imaging instrumentation settings are selected from the group consisting of depth of field, gain, and monitor intensity.

8. The method according to claim 4, wherein the head is maintained in a 45 degree counter-rotated position by a head block.

9. The method according to claim 4, further comprising the step of performing an intima-media thickness measurement on a length the far wall portion of the carotid artery.

10. The method according to claim 9, wherein the intima-media thickness measurement is performed along a 1 centimeter length of the far wall portion of the carotid artery.

11. The method according to claim 1, wherein the transducer is rotated through about 90 degrees around the approximate vertical axis, so as to develop a longitudinal image view along a length of the carotid artery, such that an ultrasound beam is directed in an aspect approximately perpendicular to an arterial wall such that a reflected signal from intima-media complex is maximized, the ultrasound beam further directed in an aspect parallel to the arterial vessel wall such that gaps in the reflected signal from the intima-media complex are minimized.

12. A standardized method for acquiring an accurate and reproducible vascular image and obtaining accurate and reproducible measurements of vascular structures, the method comprising:

performing an ultrasonographic examination of a vascular structure;

acquiring an ultrasonographic image of a particular region of the vascular structure under examination, the acquiring step including;

positioning an ultrasound transducer so as to develop a transverse image view through a neck section chosen to contain a visualization of a carotid artery and a jugular vein;

displaying the transverse view on a split-screen display;

manipulating transducer position and angulation until the jugular vein and carotid artery are displayed in a substantially vertical stack orientation, the stack defining an approximate vertical axis though a center of the jugular and a center of the carotid; and rotating the transducer through about 90 degrees around the approximate vertical axis, so as to develop a longitudinal image view along a length of the carotid artery, while maintaining the jugular vein and the carotid artery in the substantially stacked orientation;

displaying the acquired image on a first half portion of a split-screen display;

recalling an ultrasonographic image of said particular region of the vascular structure captured during a previously performed ultrasound examination;

displaying the recalled image on a second half portion of the split-screen display;

comparing the acquired image to the recalled image; and adjusting an ultrasonographic transducer orientation until the acquired image substantially matches the recalled image.

13. The method according to claim 12, wherein the transducer is rotated through about 90 degrees around the approximate vertical axis, so as to develop a longitudinal image view along a length of the carotid artery, such that an ultrasound beam is directed in an aspect approximately perpendicular to an arterial wall such that a reflected signal from an intima-media complex is maximized, the ultrasound beam further directed in an aspect parallel to the arterial vessel axis such that gaps in the reflected signal from the intima-media complex are minimized.

14. The method according to claim 13, wherein each longitudinal view includes anatomical landmarks for reproducing transducer angulation, the anatomical landmarks including a portion of a carotid artery bulb structure, each longitudinal view further including an image of at least a length of a far wall portion of the carotid artery distal to the carotid artery bulb portion.

15. The method according to claim 14, further comprising:
retrieving a set of display characteristic parameters of ultrasound imaging instrumentation settings associated to the previous obtained longitudinal image, the instrumentation settings including depth of field, gain, and monitor intensity; and
replicating the ultrasound imaging instrumentation settings on the display for the real-time longitudinal image.

16. The method according to claim 15, further comprising acquiring an ECG trace in simultaneous fashion with the acquisition of the real-time longitudinal image, an ECG trace being acquired in substantially similar fashion for the retrieved previously obtained longitudinal image; and
displaying the corresponding ECG trace with the respective longitudinal image, each ECG trace defining a time index such that real-time and previous longitudinal images are displayed at substantially the same time during a cardiac cycle.

17. The method according to claim 16, wherein each length of a far wall portion of the carotid artery distal to the carotid artery bulb portion is approximately 1 centimeter in length, and each is selected from a substantially similar location, on each of the real-time and previous longitudinal images.

18. A system for acquiring standardized accurate and reproducible ultrasound visualizations of anatomical structure comprising:
an ultrasonogram system operating in B-mode and including a transducer, the transducer acquiring ultrasound images in a plane oriented in accord with a major axis of the transducer;
an image recording system adapted to receive and record images acquired by the ultrasonogram system;
a computer processor, including an image digitizer, the processor coupled to the ultrasonogram system and the image recording system and displaying digitized ultrasound images;
an image analysis application hosted on the computer processor, the image analysis application allocating a digitized ultrasound image taken during a present examination procedure to a first screen location of a split-screen display, the image analysis application retrieving a digitized ultrasound image taken during a previous examination procedure and allocating the retrieved image to a second screen location of the split-screen display;
a first ultrasound image visualization, the first image including a visualization of a transverse view of a jugular vein and a carotid artery disposed in a substantially vertical stack orientation, the stack defining an approximate vertical axis through a center of the jugular and a center of the carotid; and
a second ultrasound image visualization, the second image including a visualization of a longitudinal view along a length of the carotid artery by rotating the transducer through about 90 degrees around the approximate vertical axis while maintaining the jugular vein and the carotid artery in the substantially stacked orientation.

19. The system according to claim 18, wherein each longitudinal view includes anatomical landmarks for reproducing transducer angulation, the anatomical landmarks including a portion of a carotid artery bulb structure, each longitudinal view further including an image of at least a length of a far wall portion of the carotid artery distal to the carotid artery bulb portion.

20. The system according to claim 19, further comprising:
an ECG, coupled to the system, the ECG developing a trace in simultaneous fashion with the acquisition of ultrasound images, an ECG trace being acquired in substantially similar fashion for the retrieved previously obtained image; and
a time coder, the time coder providing a unique time code reference for each acquired ultrasound image.

21. A method for accurately replicating ultrasound images of vascular structure, taken at spaced-apart examination intervals, so as to develop a set of substantially congruent sequential images of the vascular structure, the method comprising:
obtaining a first ultrasound image of a longitudinal section of a carotid artery by manipulating an ultrasound probe, the probe positioned to develop an image including selected anatomical structures oriented to define a position reference;
storing the first ultrasound image as a prior examination image in a memory store;
obtaining a second ultrasound image of a longitudinal section of a carotid artery, by manipulating an ultrasound probe, the probe positioned to develop the second image so as to include said selected anatomical structures;
retrieving the first image from the memory store;
displaying the first and second images side-by-side on a split screen display; and
manipulating transducer position and angulation until the selected anatomical structures of the second image substantially match the selected anatomical structures of the first image, wherein the selected anatomical structures include a jugular vein and carotid artery displayed in a substantially vertical stack orientation, the first and second images each defining a longitudinal image view along a length of the carotid artery, while maintaining the jugular vein and the carotid artery in the substantially stacked orientation.

22. The method according to claim 21, wherein the selected anatomical structures include a visualization of a carotid bulb portion proximate the longitudinal image view along the length of the carotid artery.

* * * * *